US010815539B1

(12) United States Patent
Brambati et al.

(10) Patent No.: US 10,815,539 B1
(45) Date of Patent: Oct. 27, 2020

(54) ASSAYS FOR THE DETECTION OF SARS-COV-2

(71) Applicant: DiaSorin S.p.A., Saluggia (Vercelli) (IT)

(72) Inventors: Chiara Brambati, Saluggia (IT); Simone Bocchetta, Saluggia (IT); Giulia Minnucci, Saluggai (IT)

(73) Assignee: DiaSorin S.p.A., Saluggia (IT)

( * ) Notice: Subject to any disclaimer, the term of this patent is extended or adjusted under 35 U.S.C. 154(b) by 0 days.

(21) Appl. No.: 16/837,364

(22) Filed: Apr. 1, 2020

(30) Foreign Application Priority Data

Mar. 31, 2020 (IT) ........................ 102020000006754

(51) Int. Cl.

| | |
|---|---|
| ***C12Q 1/68*** | (2018.01) |
| ***C12Q 1/70*** | (2006.01) |
| ***C12Q 1/48*** | (2006.01) |
| ***C12N 15/11*** | (2006.01) |

(52) U.S. Cl.
CPC .............. *C12Q 1/701* (2013.01); *C12N 15/11* (2013.01); *C12Q 1/48* (2013.01)

(58) Field of Classification Search
None
See application file for complete search history.

(56) References Cited

U.S. PATENT DOCUMENTS

| | | | |
|---|---|---|---|
| 7,393,638 | B2 | 7/2008 | Chou |
| 7,399,588 | B2 | 7/2008 | Minekawa et al. |
| 7,527,967 | B2 | 5/2009 | Chao et al. |
| 7,566,533 | B2 | 7/2009 | Jacobs et al. |
| 7,582,740 | B2 | 9/2009 | Briese et al. |
| 7,622,112 | B2 | 11/2009 | Berry et al. |
| 7,709,188 | B2 | 5/2010 | Kostrikis |
| 7,736,850 | B2 | 6/2010 | Van Der Werf et al. |
| 8,142,997 | B2 | 3/2012 | Scholl et al. |
| 8,343,718 | B2 | 1/2013 | Van Der Werf et al. |
| 8,445,650 | B2 | 3/2013 | Simpson et al. |
| 8,541,003 | B2 | 9/2013 | Anderson et al. |
| 8,784,829 | B2 | 7/2014 | Morsey et al. |
| 9,067,205 | B2 | 6/2015 | Ludowise et al. |
| 9,132,423 | B2 | 9/2015 | Battrell et al. |

(Continued)

FOREIGN PATENT DOCUMENTS

| | | |
|---|---|---|
| EP | 1694829 | 8/2010 |
| EP | 1690207 | 9/2010 |

(Continued)

OTHER PUBLICATIONS

Jung et al., Comparative analysis of primer-probe sets for the laboratory confirmation of SARS-CoV-2, bioRxiv 2020.02.25.964775; doi: https://doi.org/10.1101/2020.02.25.964775, Feb. 27, 2020.*

(Continued)

*Primary Examiner* — Aaron A Priest
(74) *Attorney, Agent, or Firm* — Jeffrey I. Auerbach; AuerbachSchrot LLC

(57) ABSTRACT

The present invention is directed to methods for assaying for the presence of SARS-CoV-2 in a sample, including a clinical sample, and to oligonucleotides, reagents and kits useful in such assays. In particular, the present invention is directed to such assays that are rapid, accurate and specific for the detection of SARS-CoV-2.

30 Claims, 2 Drawing Sheets

Specification includes a Sequence Listing.

(56) References Cited

U.S. PATENT DOCUMENTS

| | | | |
|---|---|---|---|
| 9,945,856 | B2 | 4/2018 | van der Hoek |
| 2005/0095618 | A1 | 5/2005 | Tsui et al. |
| 2005/0136480 | A1 | 6/2005 | Brahmachari et al. |
| 2005/0208066 | A1 | 9/2005 | Chao et al. |
| 2006/0286124 | A1 | 12/2006 | Burt et al. |
| 2007/0092938 | A1 | 4/2007 | Kwang et al. |
| 2008/0081047 | A1 | 4/2008 | Berry et al. |
| 2008/0090224 | A1 | 4/2008 | Yu et al. |
| 2010/0233250 | A1 | 9/2010 | Baras et al. |
| 2010/0279273 | A1 | 11/2010 | Bergeron et al. |
| 2010/0285457 | A1 | 11/2010 | Peiris et al. |
| 2011/0159001 | A1 | 6/2011 | Lanzavecchia |
| 2011/0262892 | A1 | 10/2011 | Aoyagi et al. |
| 2012/0045469 | A1 | 2/2012 | Baras et al. |
| 2012/0291565 | A1 | 11/2012 | Ludowise et al. |
| 2016/0238601 | A1 | 8/2016 | Baric et al. |
| 2018/0326044 | A1 | 11/2018 | Carter |

FOREIGN PATENT DOCUMENTS

| | | |
|---|---|---|
| EP | 2275534 | 1/2011 |
| EP | 2361974 | 8/2011 |
| EP | 1697507 | 9/2012 |
| EP | 2597162 | 5/2013 |
| EP | 2709760 | 6/2019 |
| EP | 2499498 | 7/2019 |
| WO | WO 2004/097021 | 11/2004 |
| WO | WO 2005/054469 | 6/2005 |
| WO | WO 2005/056584 | 6/2005 |
| WO | WO 2005/057464 | 6/2005 |
| WO | WO 2006/068663 | 6/2006 |
| WO | WO 2008/155316 | 12/2008 |
| WO | WO 2009/085025 | 7/2009 |
| WO | WO 2009/128963 | 10/2009 |
| WO | WO 2010/063685 | 6/2010 |
| WO | WO 2011/059443 | 5/2011 |

OTHER PUBLICATIONS

WHO, attached, available at https://www.who.int/nepal/activities/supporting-elimination-of-kala-azar-as-a-public-health-problem/docs/default-source/coronaviruse/whoinhouseassays, published Mar. 31, 2020.*

Northill & Mackay, Severe acute respiratory syndrome coronavirus 2 (SARS-CoV-2) real-time RT-PCR ORF1ab 2020, dx.doi.org/10.17504/protocols.io.bchvit66, Feb. 13, 2020.*

Li et al., High sensitivity detection of SARS-CoV-2 using multiplex PCR and a multiplex-PCR-based metagenomic method, Preprint from bioRxiv, Mar. 13, 2020 DOI: 10.1101/2020.03.12.988246.*

Chan et al., A Familial Cluster of Pneumonia Associated With the 2019 Novel Coronavirus Indicating Person-To-Person Transmission: A Study of a Family Cluster, Lancet Feb. 15, 2020;395(10223):514-523. doi: 10.1016/S0140-6736(20)30154-9. Epub Jan. 24, 2020.*

Lu et al., SARS-CoV-2 detection using digital PCR for COVID-19 diagnosis, treatment monitoring and criteria for discharge, medRxiv 2020.03.24.20042689; doi: https://doi.org/10.1101/2020.03.24.20042689, Mar. 20, 2020.*

Al Johani, S. et al. (2016) "*MERS-CoV Diagnosis: An Update*," J. Infect. Public Health 9(3):216-219.

Brüssow, H. (2020) "*The Novel Coronavirus—A Snapshot of Current Knowledge*," Microbial Biotechnology 0:(0):1-6.

Chan, J.F. et al. (2013) "*Interspecies Transmission And Emergence Of Novel Viruses: Lessons From Bats And Birds*," Trends Microbiol. 21(10):544-555.

Chan, J.F. et al. (2020) "*Genomic Characterization Of The 2019 Novel Human-Pathogenic Coronavirus Isolated From A Patient With Atypical Pneumonia After Visiting Wuhan*," Emerg. Microbes. Infect. 9(1):221-236.

Chan, J.F. et al. (2020) "*Improved Molecular Diagnosis Of COVID-19 By The Novel, Highly Sensitive And Specific COVID-19-RdRp/Hel Real-Time Reverse Transcription-Polymerase Chain Reaction Assay Validated In Vitro And With Clinical Specimens*," J Clin. Microbiol. JCM.00310-20. doi: 10.1128/JCM.00310-20; pp. 1-33.

Chen, Y, et al. (2020) "*Emerging Coronaviruses: Genome Structure, Replication, And Pathogenesis*," J. Med. Virol. 92:418-423.

Chen, Y. et al. (2020) "*Structure Analysis Of The Receptor Binding Of 2019-Ncov*," Biochem. Biophys. Res. Commun. 525:135-140.

Cordes, A.K. et al. (2020) "*Rapid Random Access Detection Of The Novel SARS-Coronavirus-2 (SARS-CoV-2, Previously 2019-nCoV) Using An Open Access Protocol For The Panther Fusion*," J. Clin. Virol. 125:104305 doi: 10.1016/j.jcv.2020.104305; pp. 1-2.

Corman, V.M. et al. (2020) "*Detection Of 2019 Novel Coronavirus (2019-nCoV) By Real-Time RT-PCR*," Eurosurveill. 25(3):2000045; pp. 1-8.

DHHS Press Release (Mar. 13, 2020) "*HHS Funds Development of COVID-19-19 Diagnostic Tests*," https://www.hhs.gov/about/news/2020/03/13/hhs-funds-development-covid-19-diagnostic-tests.html 2 pages.

DiaSorin Liaison MDX Product Brochure (2018); pp. 1-4.

DiaSorin Press Release (Mar. 30, 2020) "*DiaSorin Molecular COVID-19 Test Has Received FDA Emergency Use Authorization*," https://molecular.diasorin.com/international/wp-content/uploads/2020/03/DiaSorin-Molecular-COVID-19-EUA-APPROVED.pdf (3 pages).

Dreier, J. et al. (2005) "*Use of Bacteriophage MS2 as an Internal Control in Viral Reverse Transcription-PCR Assays*," J. Clin. Microbiol. 43(9):4551-4557.

Drosten et al. (2003) "*Identification Of A Novel Coronavirus In Patients With Severe Acute Respiratory Syndrome*," New Engl. J. Med. 348:1967-1976.

Fang, Y. et al. (2020) "*Transmission Dynamics Of The COVID-19 Outbreak And Effectiveness Of Government Interventions: A Data-Driven Analysis*," J. Med. Virol. doi: 10.1002/jmv.25750.

Fluorophores and BHQ (2019) Biosearch Technologies; 1 page.

Gasparic, M.B et al. (2010) "*Comparison Of Nine Different Real-Time PCR Chemistries For Qualitative And Quantitative Applications In GMO Detection*," Anal. Bioanal. Chem. 396(6):2023-2029.

GenBank Accession No. NC_002645.1 (Human coronavirus 229E) (2018) 12 pages.

GenBank Accession No. NC_004718.3 (SARS-coronavirus) (2018) 18 pages.

GenBank Accession No. NC_005831.2 (Human Coronavirus NL63) (2018) 11 pages.

GenBank Accession No. NC_006213.1 (Human coronavirus OC43 strain ATCC VR-759) (2019) 13 pages.

GenBank Accession No. NC_006577.2 (Human coronavirus HKU1) (2018) 14 pages.

GenBank Accession No. NC_019843.3 (Middle East Respiratory Syndrome coronavirus) (2018) 16 pages.

GenBank Accession No. NC_045512.2 (SARS-CoV-2) (2020) 16 pages.

Ghannam, M,G, et al. (2020) "*Biochemistry, Polymerase Chain Reaction (PCR)*," StatPearls Publishing, Treasure Is.; pp. 1-4.

Goel, G. et al. (2005) "*Molecular Beacon: A Multitask Probe*," J. Appl. Microbiol. 99(3):435-442.

Gong, S.R. et al. (2018) "*The Battle Against SARS And MERS Coronaviruses: Reservoirs And Animal Models*," Animal Model Exp. Med. 1(2):125-13.

Han, S.X. et al. (2013) "*Molecular Beacons: A Novel Optical Diagnostic Tool*," Arch. Immunol. Ther. Exp. (Warsz). 61(2):139-148.

He, Y. et al. (2004) *Receptor-Binding Domain Of SARS-CoV Spike Protein Induces Highly Potent Neutralizing Antibodies: Implication For Developing Subunit Vaccine*, Biochem. Biophys. Res. Commun. 324:773-781.

Holland, P.M. et al. (1991) "*Detection Of Specific Polymerase Chain Reaction Product By Utilizing The 5'→3' Exonuclease Activity Of Thermus Aquaticus DNA Polymerase*," Proc. Natl. Acad. Sci. (U.S.A.) 88(16):7276-7280.

Ji, W. et al. (2020) "*Cross-Species Transmission Of The Newly Identified Coronavirus 2019-nCoV*," J Med. Virol. 92:433-440.

Ju, J. et al. (1995) "*Fluorescence Energy Transfer Dye-Labeled Primers For DNA Sequencing And Analysis*," Proc. Natl. Acad. Sci. (USA) 92:4347-4351.

(56) References Cited

OTHER PUBLICATIONS

Kong, I. et al. (2020) "*Early Epidemiological and Clinical Characteristics of 28 Cases of Coronavirus Disease in South Korea*," Osong Public Health Res Perspect. 11(1):8-14.
Kralik, P. et al. (2017) "*A Basic Guide to Real-Time PCR in Microbial Diagnostics: Definitions, Parameters, and Everything*," Front. Microbiol. 8:108; pp. 1-9.
Lai, C.C. et al. (2020) "*Severe Acute Respiratory Syndrome Coronavirus 2 (SARS-CoV-2) And Coronavirus Disease-2019 (COVID-19): The Epidemic And The Challenges*," Int. J. Antimicrob. Agents. 55(3):105924; pp. 1-9.
Li, F. (2016) "*Structure, Function, And Evolution Of Coronavirus Spike Proteins*," Annu. Rev. Virol. 3:237-261.
Li, Q. et al. (2020) "*Early Transmission Dynamics In Wuhan, China, Of Novel Coronavirus-Infected Pneumonia*," New Engl. J. Med. DOI: 10.1056/NEJMoa2001316; pp. 1-9.
Li, Z. et al. (2020) "*Development and Clinical Application of A Rapid IgM-IgG Combined Antibody Test for SARS-CoV-2 Infection Diagnosis*," J. Med. Virol. doi: 10.1002/jmv.25727; pp. 1-16.
Liu, R. et al. (2020) "*Positive Rate Of RT-PCR Detection Of SARS-CoV-2 Infection In 4880 Cases From One Hospital In Wuhan, China, From Jan.-Feb. 2020*," Clinica Chimica Acta 505:172-175.
Lorenz, T.C. (2012) "*Polymerase Chain Reaction: Basic Protocol Plus Troubleshooting And Optimization Strategies*," J. Vis. Exp. May 22, 2012;(63):e3998; pp. 1-15.
Lu, G. et al. (2015) "*Bat-To-Human: Spike Features Determining 'Host Jump' Of Coronaviruses SARS-CoV, MERS-CoV, And Beyond*," Trends Microbiol. 23:468-478.
Lu, R. et al. (2020) "*Genomic Characterisation And Epidemiology Of 2019 Novel Coronavirus: Implications For Virus Origins And Receptor Binding*," Lancet 395(10224):565-574.
Mackay, I.M. (2015) "*MERS Coronavirus: Diagnostics, Epidemiology And Transmission*," Virol. J. 12:222. doi: 10.1186/s12985-015-0439-5; pp. 1-21.
Marra, M.A. et al. (2003) "*The Genome Sequence of the SARS-Associated Coronavirus*," Science 300(5624):1399-1404.
Masters, P.S. (2006) "*The Molecular Biology Of Coronaviruses*," Adv. Virus Res. 66:193-292.
Navarro, E. et al. (2015) "*Real-Time PCR Detection Chemistry*," Clin. Chim. Acta 439:231-250.
Pang, J. et al. (2020) "*Potential Rapid Diagnostics, Vaccine and Therapeutics for 2019 Novel Coronavirus (2019-nCoV): A Systematic Review*," J. Clin. Med. 26;9(3)E623; pp. 1-33.
Peake, I. (1989) "*The Polymerase Chain Reaction*," J. Clin. Pathol. ;42(7):673-676.
Pfefferle, S. et al. (2020) "*Evaluation Of A Quantitative RT-PCR Assay For The Detection Of The Emerging Coronavirus SARS-CoV-2 Using A High Throughput System*," Euro. Surveill. 25(9) doi: 10.2807/1560-7917.ES.2020.25.9.2000152; pp. 1-5.
Quenchers Design and Protocols (2020) Gene Link Web Brochure; 3 pages.
Sah, R. et al. (2020) "*Complete Genome Sequence of a 2019 Novel Coronavirus (SARS-CoV-2) Strain Isolated in Nepal*," Microbiol. Resource Announcements 9(11): e00169-20, pp. 1-3.
SantaLucia, J. (1998) *A Unified View of Polymer, Dumbbell, And Oligonucleotide DNA Nearest-Neighbor Thermodynamics*, Proc. Natl. Acad. Sci. (U.S.A.) 95:1460-1465.
Sigma Aldrich (2014) "*Primers and Fluorescent Probes* For Real-Time PCR and Other Applications," Product Brochure; pp. 1-20.
Spiteri, G. et al. (2020) "*First Cases Of Coronavirus Disease 2019 (COVID-19) In The WHO European Region, Jan. 24-Feb. 21, 2020*," Eurosurveill. 25(9) doi: 10.2807/1560-7917.ES.2020.25.9.2000178; pp. 1-11.
Su, S. et al. (2016) "*Epidemiology, Genetic Recombination, And Pathogenesis Of Coronaviruses*," Trends Microbiol. 24:490-502.
Tang, A. et al. (2020) "*Detection of Novel Coronavirus by RT-PCR in Stool Specimen from Asymptomatic Child, China*," Emerg Infect Dis. 26(6):pp. 1-7.
Von Ahsen, N. et al. (1999) "*Application Of A Thermodynamic Nearest-Neighbor Model To Estimate Nucleic Acid Stability And Optimize Probe Design: Prediction Of Melting Points Of Multiple Mutations Of Apolipoprotein B-3500 And Factor V With A Hybridization Probe Genotyping Assay On The Lightcycler*," Clin. Chem. 45(12):2094-2101.
Wang, C. et al. (2020) "*The Establishment Of Reference Sequence For SARS-CoV-2 And Variation Analysis*," J. Med. Virol. doi: 10.1002/jmv.25762; pp. 1-8.
Wang, Q. et al. (2016) "*MERS-CoV Spike Protein: Targets For Vaccines And Therapeutics*," Antiviral. Res. 133:165-177.
Wang, W. et al. (2020) "*Detection of SARS-CoV-2 in Different Types of Clinical Specimens*," JAMA doi: 10.1001/jama.2020.3786; pp. 1-2.
Whitcombe, D. et al. (1999) "*Detection Of PCR Products Using Self-Probing Amplicons And Fluorescence*," Nat. Biotechnol. 17(8):804-807.
Won, J. et al. (2020) "*Development Of A Laboratory-Safe And Low-Cost Detection Protocol For SARS-CoV-2 Of The Coronavirus Disease 2019 (COVID-19)*," Exp. Neurobiol. 29(2):pp. 1-13.
Wu, X. et al. (2020) "*Co-infection with SARS-CoV-2 and Influenza A Virus in Patient with Pneumonia, China*," Emerg Infect Dis. 26(6 26(6); pp. 1-7.
Xie, C. et al. (2020) "*Comparison Of Different Samples For 2019 Novel Coronavirus Detection By Nucleic Acid Amplification Tests*" Int. J. Infect. Dis. /doi.org/10.1016/j.ijid.2020.02.050; pp. 1-12.
Xu, K. et al. (2020) "*Management Of Corona Virus Disease-19 (COVID-19): The Zhejiang Experience*," Zhejiang Da Xue Bao Yi Xue Ban. 49(1):0; Abstract Only; pp. 1-2.
Yin, Y. et al. (2018) "*MERS, SARS And Other Coronaviruses As Causes Of Pneumonia*," Respirology 23(2):130-137.
Zearfoss, N.R. et al. (2012) "*End-Labeling Oligonucleotides with Chemical Tags After Synthesis*," Meth. Mol. Biol. 941:181-193.
Zhang, W. et al. (2020) "*Molecular And Serological Investigation Of 2019-nCoV Infected Patients: Implication Of Multiple Shedding Routes*," Emerg. Microbes Infect. 9(1):386-389.
Zhao, W.M. et al. (2020) "*The 2019 Novel Coronavirus Resource*," Yi Chuan. 42(2):212-221; Abstract Only; pp. 1-2.
Zheng, J. et al. (2015) ("*Rationally Designed Molecular Beacons For Bioanalytical And Biomedical Applications*," Chem. Soc. Rev. 44(10):3036-3055.
Zhou, Y. et al. (2020) "*Network-Based Drug Repurposing For Novel Coronavirus 2019-nCoV/SARS-CoV-2*," Cell Discov. 6(14): doi.org/10.1038/s41421-020-0153-3; pp. 1-18.
Zhu, N. et al. (2020) "*A Novel Coronavirus from Patients with Pneumonia in China, 2019*," New Engl. J. Med. 382(8):727-733.

* cited by examiner

SEQUENCE LISTING

```
<160> NUMBER OF SEQ ID NOS: 15

<210> SEQ ID NO 1
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Preferred Forward ORF1ab Gene Primer

<400> SEQUENCE: 1

atggtagagt tgatggtcaa                                              20


<210> SEQ ID NO 2
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Preferred Reverse ORF1ab Gene Primer
```

```
<400> SEQUENCE: 2

taagactagc ttgtttggga                                                   20


<210> SEQ ID NO 3
<211> LENGTH: 117
<212> TYPE: DNA
<213> ORGANISM: SARS-CoV2 Coronavirus
<220> FEATURE:
<221> NAME/KEY: misc_feature
<222> LOCATION: (1)..(117)
<223> OTHER INFORMATION: Amplified Region of ORF1ab Gene ("Sense"
      Strand)

<400> SEQUENCE: 3

atggtagagt tgatggtcaa gtagacttat ttagaaatgc ccgtaatggt gttcttatta      60

cagaaggtag tgttaaaggt ttacaaccat ctgtaggtcc caaacaagct agtctta        117


<210> SEQ ID NO 4
<211> LENGTH: 117
<212> TYPE: DNA
<213> ORGANISM: SARS-CoV2 Coronavirus
<220> FEATURE:
<221> NAME/KEY: misc_feature
<222> LOCATION: (1)..(117)
<223> OTHER INFORMATION: Amplified Region of ORF1ab Gene ("Anti-Sense"
      Strand)

<400> SEQUENCE: 4

taagactagc ttgtttggga cctacagatg gttgtaaacc tttaacacta ccttctgtaa      60

taagaacacc attacgggca tttctaaata agtctacttg accatcaact ctaccat        117


<210> SEQ ID NO 5
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Preferred Forward S Gene Primer

<400> SEQUENCE: 5

ctaaccaggt tgctgttctt                                                   20


<210> SEQ ID NO 6
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Preferred Reverse S Gene Primer

<400> SEQUENCE: 6

cctgtagaat aaacacgcca                                                   20


<210> SEQ ID NO 7
<211> LENGTH: 103
<212> TYPE: DNA
<213> ORGANISM: SARS-CoV2 Coronavirus
<220> FEATURE:
<221> NAME/KEY: misc_feature
<222> LOCATION: (1)..(103)
<223> OTHER INFORMATION: Amplified Region of S Gene ("Sense" Strand)

<400> SEQUENCE: 7

ctaaccaggt tgctgttctt tatcaggatg ttaactgcac agaagtccct gttgctattc      60
```

atgcagatca acttactcct acttggcgtg tttattctac agg 103

<210> SEQ ID NO 8
<211> LENGTH: 103
<212> TYPE: DNA
<213> ORGANISM: SARS-CoV2 Coronavirus
<220> FEATURE:
<221> NAME/KEY: misc_feature
<222> LOCATION: (1)..(103)
<223> OTHER INFORMATION: Amplified Region of S Gene ("Anti-Sense" Strand)

<400> SEQUENCE: 8
cctgtagaat aaacacgcca agtaggagta agttgatctg catgaatagc aacagggact 60
tctgtgcagt taacatcctg ataaagaaca gcaacctggt tag 103

<210> SEQ ID NO 9
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: Preferred ORF1ab Gene Probe

<400> SEQUENCE: 9
tgcccgtaat ggtgttctta ttacaga 27

<210> SEQ ID NO 10
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: Complement of Preferred ORF1ab Probe

<400> SEQUENCE: 10
tctgtaataa gaacaccatt acgggca 27

<210> SEQ ID NO 11
<211> LENGTH: 21
<212> TYPE: DNA
<213> ORGANISM: SARS-CoV2 Coronavirus
<220> FEATURE:
<221> NAME/KEY: misc_feature
<223> OTHER INFORMATION: Preferred S Gene Probe

<400> SEQUENCE: 11
tgcacagaag tccctgttgc t 21

<210> SEQ ID NO 12
<211> LENGTH: 21
<212> TYPE: DNA
<213> ORGANISM: SARS-CoV2 Coronavirus
<220> FEATURE:
<221> NAME/KEY: misc_feature
<223> OTHER INFORMATION: Complement of Preferred S Gene Probe

<400> SEQUENCE: 12
agcaacaggg acttctgtgc a 21

<210> SEQ ID NO 13
<211> LENGTH: 16
<212> TYPE: DNA
<213> ORGANISM: Bacteriophage MS2

-continued

```
<220> FEATURE:
<221> NAME/KEY: misc_feature
<222> LOCATION: (1)..(16)
<223> OTHER INFORMATION: Forward MS2 Phage Internal Control Primer

<400> SEQUENCE: 13

tgctcgcgga tacccg                                                   16


<210> SEQ ID NO 14
<211> LENGTH: 20
<212> TYPE: DNA
<213> ORGANISM: Bacteriophage MS2
<220> FEATURE:
<221> NAME/KEY: misc_feature
<223> OTHER INFORMATION: Reverse MS2 Phage Internal Control Primer

<400> SEQUENCE: 14

aacttgcgtt ctcgagcgat                                               20


<210> SEQ ID NO 15
<211> LENGTH: 24
<212> TYPE: DNA
<213> ORGANISM: Bacteriophage MS2
<220> FEATURE:
<221> NAME/KEY: misc_feature
<222> LOCATION: (1)..(24)
<223> OTHER INFORMATION: MS2 Phage Internal Control Probe

<400> SEQUENCE: 15

acctcgggtt tccgtcttgc tcgt                                          24
```

ASSAYS FOR THE DETECTION OF SARS-COV-2

CROSS-REFERENCE TO RELATED APPLICATIONS

This application claims priority to Italian Patent Application No. 102020000006754, filed on Mar. 31, 2020 (pending), which application is herein incorporated by reference in its entirety.

REFERENCE TO SEQUENCE LISTING

This application includes one or more Sequence Listings pursuant to 37 C.F.R. 1.821 et seq., which are disclosed in computer-readable media (file name: SARS-CoV-2_0400_0020_ST25.txt, created on Mar. 24, 2020, and having a size of 4304 bytes), which file is herein incorporated by reference in its entirety.

FIELD OF THE INVENTION

The present invention is directed to methods for assaying for the presence of SARS-CoV-2 in a sample, including a clinical sample, and to oligonucleotides, reagents and kits useful in such assays. In particular, the present invention is directed to such assays that are rapid, accurate and specific for the detection of SARS-CoV-2.

BACKGROUND OF THE INVENTION

I. SARS-CoV-2

Severe Acute Respiratory Syndrome Coronavirus 2 (SARS-CoV-2) is a newly identified coronavirus species (the virus was previously provisionally named "2019 novel coronavirus" or "2019-nCoV"). SARS-CoV-2 infection is spread by human-to-human transmission via droplets or direct contact, and infection has been estimated to have a mean incubation period of 6.4 days and a Basic Reproduction Number of 2.24-3.58 (i.e., an epidemic doubling time of 6-8 days) (Fang, Y. et al. (2020) "*Transmission Dynamics Of The COVID*-19 *Outbreak And Effectiveness Of Government Interventions: A Data-Driven Analysis*," J. Med. Virol. doi: 10.1002/jmv.25750; Zhao, W. M. et al. (2020) "*The* 2019 *Novel Coronavirus Resource*," Yi Chuan. 42(2):212-221; Zhu, N. et al. (2020) "*A Novel Coronavirus from Patients with Pneumonia in China,* 2019," New Engl. J. Med. 382 (8):727-733).

Patients infected with SARS-CoV-2 exhibit COVID-19, a condition initially characterized by fever and cough (Kong, I. et al. (2020) "*Early Epidemiological and Clinical Characteristics of* 28 *Cases of Coronavirus Disease in South Korea*," Osong Public Health Res Perspect. 11(1):8-14). In approximately 20% of patients, COVID-19 progresses to a severe respiratory disease and pneumonia that has a mortality of 5-10% (1-2% overall mortality). Bilateral lung involvement with ground-glass opacity are the most common finding from computed tomography images of the chest (Lai, C. C. et al. (2020) "*Severe Acute Respiratory Syndrome Coronavirus* 2 (*SARS-CoV*-2) *And Coronavirus Disease*-2019 (*COVID*-19): *The Epidemic And The Challenges*," Int. J. Antimicrob. Agents. 55(3):105924). Since a cure for COVID-19 has not yet been identified, treatment presently consists of a "Four-Anti and Two-Balance" strategy included antivirus, anti-shock, anti-hyoxemia, anti-secondary infection, and maintaining water, electrolyte and acid-base balance and microecological balance (Xu, K. et al. (2020) "*Management Of Corona Virus Disease*-19 (*COVID*-19): *The Zhejiang Experience*," Zhejiang Da Xue Bao Yi Xue Ban. 49(1):0).

Coronaviruses (CoVs) belong to the subfamily Orthocoronavirinae in the family Coronaviridae and the order Nidovirales. The Coronaviridae family of viruses are enveloped, single-stranded, RNA viruses that possess a positive-sense RNA genome of 26 to 32 kilobases in length. Four genera of coronaviruses have been identified, namely, Alphacoronavirus (αCoV), Betacoronavirus (βCoV), Deltacoronavirus (δCoV), and Gammacoronavirus (γCoV) (Chan, J. F. et al. (2013) "*Interspecies Transmission And Emergence Of Novel Viruses: Lessons From Bats And Birds*," Trends Microbiol. 21(10):544-555). Evolutionary analyses have shown that bats and rodents are the gene sources of most αCoVs and βCoVs, while avian species are the gene sources of most CoVs and γCoVs.

Prior to 2019, only six coronavirus species were known to be pathogenic to humans. Four of these species were associated with mild clinical symptoms, but two coronaviruses, Severe Acute Respiratory Syndrome (SARS) coronavirus (SARS-CoV) (Marra, M. A. et al. (2003) "*The Genome Sequence of the SARS-Associated Coronavirus*," Science 300(5624):1399-1404) and Middle East Respiratory Syndrome (MERS) coronavirus (MERS-CoV) (Mackay, I. M. (2015) "*MERS Coronavirus: Diagnostics, Epidemiology And Transmission*," Virol. J. 12:222. doi: 10.1186/s12985-015-0439-5) were associated with human mortalities approaching 10% (Su, S. et al. (2016) "*Epidemiology, Genetic Recombination, And Pathogenesis Of Coronaviruses*," Trends Microbiol. 24:490-502; Al Johani, S. et al. (2016) "*MERS-CoV Diagnosis: An Update*," J. Infect. Public Health 9(3):216-219).

SARS-CoV-2 is closely related (88%) to two bat-derived Severe Acute Respiratory Syndrome-like coronaviruses, bat-SL-CoVZC45 and bat-SL-CoVZXC21, and is more distantly related to SARS-CoV (79%) and MERS-CoV (50%) (Xie, C. et al. (2020) "*Comparison Of Different Samples For* 2019 *Novel Coronavirus Detection By Nucleic Acid Amplification Tests*" Int. J. Infect. Dis. /doi.org/10.1016/j.ijid.2020.02.050; Mackay, I. M. (2015) "*MERS Coronavirus: Diagnostics, Epidemiology And Transmission*," Virol. J. 12:222. doi: 10.1186/s12985-015-0439-5; Gong, S. R. et al. (2018) "*The Battle Against SARS And MERS Coronaviruses: Reservoirs And Animal Models*," Animal Model Exp. Med. 1(2):125-133; Yin, Y. et al. (2018) "*MERS, SARS And Other Coronaviruses As Causes Of Pneumonia*," Respirology 23(2):130-137). Phylogenetic analysis revealed that SARS-CoV-2 fell within the subgenus Sarbecovirus of the genus Betacoronavirus, with a relatively long branch length to its closest relatives bat-SL-CoVZC45 and bat-SL-CoVZXC21, and was genetically distinct from SARS-CoV (Drosten et al. (2003) "*Identification Of A Novel Coronavirus In Patients With Severe Acute Respiratory Syndrome*," New Engl. J. Med. 348:1967-1976; Lai, C. C. et al. (2020) "*Severe Acute Respiratory Syndrome Coronavirus* 2 (*SARS-CoV*-2) *And Coronavirus Disease*-2019 (*COVID*-19): *The Epidemic And The Challenges*," Int. J. Antimicrob. Agents. 55(3):105924; Lu, R. et al. (2020) "*Genomic Characterisation And Epidemiology Of* 2019 *Novel Coronavirus: Implications For Virus Origins And Receptor Binding*," The Lancet 395(10224): 565-574; Zhou, Y. et al. (2020) "*Network-Based Drug Repurposing For Novel Coronavirus* 2019-*nCoV/SARS-CoV*-2," Cell Discov. 6(14): doi.org/10.1038/s41421-020-0153-3).

The SARS-CoV-2 genome has been sequenced from at least 170 isolates. The reference sequence is GenBank NC 045512 (Wang, C. et al. (2020) "*The Establishment Of Reference Sequence For SARS-CoV-2 And Variation Analysis*," J. Med. Virol. doi: 10.1002/jmv.25762; Chan, J. F. et al. (2020) "*Genomic Characterization Of The 2019 Novel Human-Pathogenic Coronavirus Isolated From A Patient With Atypical Pneumonia After Visiting Wuhan*," Emerg. Microbes. Infect. 9(1):221-236).

Comparisons of the sequences of multiple isolates of the virus (MN988668 and NC 045512, isolated from Wuhan, China, and MN938384.1, MN975262.1, MN985325.1, MN988713.1, MN994467.1, MN994468.1, and MN997409.1) reveal greater than 99.99% identity (Sah, R. et al. (2020) "*Complete Genome Sequence of a 2019 Novel Coronavirus (SARS-CoV-2) Strain Isolated in Nepal*," Microbiol. Resource Announcements 9(11): e00169-20, pages 1-3; Brussow, H. (2020) "*The Novel Coronavirus—A Snapshot of Current Knowledge*," Microbial Biotechnology 0:(0):1-6). The SARS-CoV-2 genome is highly similar to that of human SARS-CoV, with an overall nucleotide identity of approximately 82% (Chan, J. F. et al. (2020) "*Genomic Characterization Of The 2019 Novel Human-Pathogenic Corona Virus Isolated From A Patient With Atypical Pneumonia After Visiting Wuhan*," Emerg Microbes Infect 9:221-236; Chan, J. F. et al. (2020) "*Improved Molecular Diagnosis Of COVID-19 By The Novel, Highly Sensitive And Specific COVID-19-RdRp/Hel Real-Time Reverse Transcription-Polymerase Chain Reaction Assay Validated In Vitro And With Clinical Specimens*," J Clin. Microbiol. JCM.00310-20. doi: 10.1128/JCM.00310-20). Based on its homology to related coronaviruses, SARS-CoV-2 is predicted to encode 12 open reading frame (ORFs) coding regions (ORF1ab, S (spike protein), 3, E (envelope protein), M (matrix), 7, 8, 9, 10b, N, 13 and 14. The arrangement of these coding regions is shown in FIG. 1. Two ORFs coding regions are of particular significance to the present invention: ORF1ab and the S gene (Lu, R. et al. (2020) "*Genomic Characterisation And Epidemiology Of 2019 Novel Coronavirus: Implications For Virus Origins And Receptor Binding*," Lancet 395(10224):565-574).

A. ORF1ab

ORF1ab is composed of 21290 nucleotides and encodes an open reading frame of 7096 amino acids in length. Via a −1 ribosomal frameshift, the encoded protein is a polyprotein (pp) composed of a first segment (pp1a) of 4401 amino acid residues, and a second segment (pp1ab) of 2695 amino acid residues (Chen, Y, et al. (2020) "*Emerging Coronaviruses: Genome Structure, Replication, And Pathogenesis*," J. Med. Virol. 92:418-423; Lu, R. et al. (2020) "*Genomic Characterisation And Epidemiology Of 2019 Novel Coronavirus: Implications For Virus Origins And Receptor Binding*," Lancet 395(10224):565-574). Both segments include the same 180 amino acid long leader sequence. The polyprotein includes multiple non-structural proteins (nsp): a 638 amino acid long nsp2 protein, a 1945 amino acid long nsp3 protein, a 500 amino acid long nsp4 protein, a 306 amino acid long nsp5 protein, a 290 amino acid long nsp6 protein, an 83 amino acid long nsp7 protein, a 198 amino acid long nsp8 protein, a 113 amino acid long nsp9 single-strand binding protein, a 139 amino acid long nsp10 protein, a 923 amino acid long nsp12 RNA-dependent RNA polymerase (RdRp), a 601 amino acid long nsp13 helicase, a 527 amino acid long nsp14a2 3→5' exonuclease, a 346 amino acid long nsp15 endoRNAse, and a 298 amino acid long nsp16 2'-O-ribose-methyltransferase (Chen, Y, et al. (2020) "*Emerging Coronaviruses: Genome Structure, Replication, And Pathogenesis*," J. Med. Virol. 92:418-423; Lu, R. et al. (2020) "*Genomic Characterisation And Epidemiology Of 2019 Novel Coronavirus: Implications For Virus Origins And Receptor Binding*," Lancet 395(10224):565-574).

B. The S Gene

The S gene encodes the SARS-CoV-2 spike protein. The S protein of SARS-CoV is functionally cleaved into two subunits: the S1 domain and the S2 domain (He, Y. et al. (2004) "*Receptor-Binding Domain Of SARS-CoV Spike Protein Induces Highly Potent Neutralizing Antibodies: Implication For Developing Subunit Vaccine*," Biochem. Biophys. Res. Commun. 324:773-781). The SARS-CoV S1 domain mediates receptor binding, while the SARS-CoV S2 domain mediates membrane fusion (Li, F. (2016) "*Structure, Function, And Evolution Of Coronavirus Spike Proteins*," Annu. Rev. Virol. 3:237-261; He, Y. et al. (2004) "*Receptor-Binding Domain Of SARS-CoV Spike Protein Induces Highly Potent Neutralizing Antibodies: Implication For Developing Subunit Vaccine*, Biochem. Biophys. Res. Commun. 324:773-781). The S gene of SARS-CoV-2 may have a similar function. Thus, the spike protein of coronaviruses is considered crucial for determining host tropism and transmission capacity (Lu, G. et al. (2015) "*Bat-To-Human: Spike Features Determining 'Host Jump' Of Coronaviruses SARS-CoV, MFRS-CoV, And Beyond*," Trends Microbiol. 23:468-478; Wang, Q. et al. (2016) "*MERS-CoV Spike Protein: Targets For Vaccines And Therapeutics*," Antiviral. Res. 133:165-177). In this regard, the S2 domain of the SARS-CoV-2 spike protein shows high sequence identity (93%) with bat-SL-CoVZC45 and bat-SL-CoVZXC21, but the SARS-CoV-2 S1 domain shows a much lower degree of identity (68%) with these bat-derived viruses (Lu, R. et al. (2020) "*Genomic Characterisation And Epidemiology Of 2019 Novel Coronavirus: Implications For Virus Origins And Receptor Binding*," Lancet 395(10224):565-574). Thus, SARS-CoV-2 may bind to a different receptor than that bound by its related bat-derived viruses. It has been proposed that SARS-CoV-2 may bind to the angiotensin-converting enzyme 2 (ACE2) as a cell receptor (Lu, R. et al. (2020) "*Genomic Characterisation And Epidemiology Of 2019 Novel Coronavirus: Implications For Virus Origins And Receptor Binding*," Lancet 395(10224):565-574).

II. Assays for the Detection of SARS-CoV-2

SARS-CoV-2 was first identified in late 2019, and is believed to be a unique virus that had not previously existed. The first diagnostic test for SARS-CoV-2 used a real-time reverse transcription-PCR (rRT-PCR) assay that employed probes and primers of the SARS-CoV-2 E, N and nsp12 (RNA-dependent RNA polymerase; RdRp) genes (the "SARS-CoV-2-RdRp-P2" assay) (Corman, V. M. et al. (2020) "*Detection Of 2019 Novel Coronavirus (2019-nCoV) By Real-Time RT-PCR*," Eurosurveill. 25(3):2000045; Spiteri, G. et al. (2020) "*First Cases Of Coronavirus Disease 2019 (COVID-19) In The WHO European Region, 24 Jan. to 21 Feb. 2020*," Eurosurveill. 25(9) doi: 10.2807/1560-7917.ES.2020.25.9.2000178).

The probes employed in such assays were "TaqMan" oligonucleotide probes that were labeled with a fluorophore on the oligonucleotide's 5' terminus and complexed with a quencher on the oligonucleotide's 3' terminus. The "TaqMan" probe principle relies on the 5"→3" exonuclease activity of Taq polymerase (Peake, I. (1989) "*The Polymerase Chain Reaction*," J. Clin. Pathol.; 42(7):673-676) to cleave the dual-labeled probe when it has hybridized to a complementary target sequence. The cleavage of the molecule separates the fluorophore from the quencher and thus leads to the production of a detectable fluorescent signal.

In the SARS-CoV-2-RdRp-P2 assay of Corman, V. M. et al. (2020), the RdRp Probe 2 and the probes of the E and N genes are described as being specific for SARS-CoV-2, whereas the RdRp Probe 2 is described as being a "PanSarbeco-Probe" that detects SARS-CoV and bat-SARS-related coronaviruses in addition to SARS-CoV-2. The assay is stated to have provided its best results using the E gene and nsp12 (RdRp) gene primers and probes (5.2 and 3.8 copies per 25 μL reaction at 95% detection probability, respectively). The resulting limit of detection (LoD) from replicate tests was 3.9 copies per 25 μL reaction (156 copies/mL) for the E gene assay and 3.6 copies per 25 μL reaction (144 copies/mL) for the nsp12 (RdRp) assay. The assay was reported to be specific for SARS-CoV-2 and to require less than 60 minutes to complete.

The US Center for Disease Control and Prevention (CDC) developed an rRT-PCR based assay protocol that targeted the SARS-CoV-2 N gene (Won, J. et al. (2020) "*Development Of A Laboratory-Safe And Low-Cost Detection Protocol For SARS-CoV-*2 *Of The Coronavirus Disease* 2019 (COVID-19)," Exp. Neurobiol. 29(2) doi: 10.5607/en20009).

Pfefferle, S. et al. (2020) ("*Evaluation Of A Quantitative RT-PCR Assay For The Detection Of The Emerging Coronavirus SARS-CoV-*2 *Using A High Throughput System*," Eurosurveill. 25(9) doi: 10.2807/1560-7917.ES.2020.25.9.2000152) discloses the use of a custom-made primer/probe set targeting the E gene. The employed primers were modified with 2'-O-methyl bases in their penultimate base to prevent formation of primer dimers. ZEN double-quenched probe (IDT) were used to lower background fluorescence. The LoD was 689.3 copies/mL with 275.72 copies per reaction at 95% detection probability. The assay was reported to be specific for SARS-CoV-2 and to require less than 60 minutes.

Chan, J. F. et al. (2020) ("*Improved Molecular Diagnosis Of COVID-*19 *By The Novel, Highly Sensitive And Specific COVID-*19*-RdRp/Hel Real-Time Reverse Transcription-Polymerase Chain Reaction Assay Validated In Vitro And With Clinical Specimens*," J. Clin. Microbiol. JCM.00310-20. doi: 10.1128/JCM.00310-20) explored the use of conserved and/or abundantly expressed SARS-CoV-2 genes as preferred targets of coronavirus RT-PCR assays. Such genes include the structural S and N genes, and the non-structural RdRp gene and ORF1ab. Chan, J. F. et al. (2020) describes the development of three real-time reverse transcriptase PCR (rRT-PCR) assays targeting the RNA-dependent RNA polymerase (RdRp)/helicase (Hel), spike (S), and nucleocapsid (N) genes of SARS-CoV-2 and compares such assays to the RdRp-P2 assay of Corman, V. M. et al. The LoD of the SARS-CoV-2-RdRp/Hel assay, the SARS-CoV-2-S assay, and the SARS-CoV-2-N assay was 1.8 $TCID_{50}$/ml, while the LoD of the SARS-CoV-2-RdRp-P2 assay was 18 $TCID_{50}$/ml. The $TCID_{50}$ is the median tissue culture infectious dose.

An rt-PCR-based assay protocol targeting the E, N, S and RdRp genes was designed for specimen self-collection from a subject via pharyngeal swab. The assay required Trizol-based RNA purification, and detection was accomplished via an RT-PCR assay using SYBR Green as a detection fluor. The assay was reported to require approximately 4 hours to complete (Won, J. et al. (2020) ("*Development Of A Laboratory-Safe And Low-Cost Detection Protocol For SARS-CoV-*2 *Of The Coronavirus Disease* 2019 (COVID-19)," Exp. Neurobiol. 29(2) doi: 10.5607/en20009).

Although prior rRT-PCR assays, such as the SARS-CoV-2-RdRp-P2 assay of Corman V. M. et al., are capable of detecting SARS-CoV-2, researchers have found them to suffer from major deficiencies. In use, such prior assays have been found to require laborious batch-wise manual processing and to not permit random access to individual samples (Cordes, A. K. et al. (2020) "*Rapid Random Access Detection Of The Novel SARS-Coronavirus-*2 (*SARS-CoV-*2*, Previously* 2019*-nCoV*) *Using An Open Access Protocol For The Panther Fusion*," J. Clin. Virol. 125:104305 doi: 10.1016/j.jcv.2020.104305). Additionally, long turnaround times and complicated operations are required. These factors cause such assays to generally take more than 2-3 hours to generate results. Due to such factors, certified laboratories are required to process such assays. The need for expensive equipment and trained technicians to perform such prior rRT-PCR assays encumbers the use of such assays in the field or at mobile locations. Thus, researchers have found such prior assays to have limited suitability for use in the rapid and simple diagnosis and screening of patients required to contain an outbreak (Li, Z. et al. (2020) "*Development and Clinical Application of A Rapid IgM-IgG Combined Antibody Test for SARS-CoV-*2 *Infection Diagnosis*," J. Med. Virol. doi: 10.1002/jmv.25727).

More significantly, prior rRT-PCR assays, such as the SARS-CoV-2-RdRp-P2 assay of Corman V. M. et al., have been found to lack specificity for SARS-CoV-2 (cross-reacting with SARS-CoV or other pathogens) (Chan, J. F. et al. (2020) "*Improved Molecular Diagnosis Of COVID-*19 *By The Novel, Highly Sensitive And Specific COVID-*19*-RdRp/Hel Real-Time Reverse Transcription-Polymerase Chain Reaction Assay Validated In Vitro And With Clinical Specimens*," J. Clin. Microbiol. JCM.00310-20) and to provide a significant number of false negative results (Li, Z. et al. (2020) "*Development and Clinical Application of A Rapid IgM-IgG Combined Antibody Test for SARS-CoV-*2 *Infection Diagnosis*," J. Med. Virol. doi: 10.1002/jmv.25727).

For example, a retrospective analysis of 4880 clinically-identified COVID-19 patients. Samples obtained from the respiratory tracts of the patients were subjected to rRT-PCR amplification of the SARS-CoV-2 open reading frame 1ab (ORF1ab) and nucleocapsid protein (N) genes. Nasal and pharyngeal swabs of patients were evaluated for COVID-19 using a quantitative rRT-PCR (qRT-PCR) test. Only 38.42% (1875 of 4880) of actual COVID-19 patients were identified as positive using the rRT-PCR test. Of those testing positive, 39.80% were positive as determined by probes of the SARS-CoV-2 N gene and 40.98% were positive as determined by probes of the SARS-CoV-2 ORF1 ab (Liu, R. et al. (2020) "*Positive Rate Of RT-PCR Detection Of SARS-CoV-*2 *Infection In* 4880 *Cases From One Hospital In Wuhan, China, From January To February* 2020," Clinica Chimica Acta 505:172-175).

The study of Chan, J. F. et al. (2020) ("*Improved Molecular Diagnosis Of COVID-*19 *By The Novel, Highly Sensitive And Specific COVID-*19*-RdRp/Hel Real-Time Reverse Transcription-Polymerase Chain Reaction Assay Validated In Vitro And With Clinical Specimens*," J. Clin. Microbiol. JCM.00310-20. doi: 10.1128/JCM.00310-20) found that of 273 specimens from 15 patients with laboratory-confirmed COVID-19, only 28% were SARS-CoV-2 positive by both the SARS-CoV-2-RdRp/Hel and RdRp-P2 assays. The SARS-CoV-2-RdRp/Hel assay was more sensitive, but still confirmed only 43.6% of the patients as having SARS-CoV-2 infection.

In a different study, RNA was extracted from 1070 clinical samples of 205 patients suffering from COVID-19. Real-time reverse transcription-PCR (rRT-PCR) was then used to amplify SARS-CoV-2 ORF1ab in order to confirm the COVID-19 diagnosis (Wang, W. et al. (2020) ("*Detection of SARS-CoV-*2 *in Different Types of Clinical Specimens*,"

JAMA doi: 10.1001/jama.2020.3786). Bronchoalveolar lavage fluid specimens were reported to exhibit the highest positive rates (14 of 15; 93%), followed by sputum (72 of 104; 72%), nasal swabs (5 of 8; 63%), fibrobronchoscope brush biopsy (6 of 13; 46%), pharyngeal swabs (126 of 398; 32%), feces (44 of 153; 29%), and blood (3 of 307; 1%). None of the 72 urine specimens tested indicated a positive result. Thus, for example, pharyngeal swabs from such actual COVID-19 patients failed to accurately diagnose SARS-CoV-2 infection in 68% of those tested. Zhang, W. et al. (2020) ("*Molecular And Serological Investigation Of* 2019-*nCoV Infected Patients: Implication Of Multiple Shedding Routes*," Emerg. Microbes Infect. 9(1):386-389) also discloses the presence of SARS-CoV-2 in feces of COVID-19 patients, however, its rRT-PCR assay results showed more anal swab positives than oral swab positives in a later stage of infection, suggesting viral shedding and the capacity of the infection to be transmitted through an oral-fecal route. A similar teaching is provided by Tang, A. et al. (2020) ("*Detection of Novel Coronavirus by RT-PCR in Stool Specimen from Asymptomatic Child, China*," Emerg Infect Dis. 26(6). doi: 10.3201/eid2606.200301). This document discloses that RT-PCR assays targeting ORF1ab and nucleoprotein N gene failed to detect SARS-CoV-2 in nasopharyngeal swab and sputum samples, but were able to detect virus in stool samples.

In a further study of individuals suffering from COVID-19, repeated assays for SARS-CoV-2 were also found to report negative results (Wu, X. et al. (2020) ("*Co-infection with SARS-CoV-*2 *and Influenza A Virus in Patient with Pneumonia, China,*" 26(6):pages 1-7. The publication teaches that existing assays for SARS-CoV-2 lack sufficient sensitivity, and thus lead to false negative diagnoses.

In light of the deficiencies encountered in using prior rRT-PCR assays, such as the SARS-CoV-2-RdRp-P2 assay of Corman V. M. et al., other approaches to assaying for SARS-CoV-2 have been explored. Li, Z. et al. (2020) ("*Development and Clinical Application of A Rapid IgM-IgG Combined Antibody Test for SARS-CoV-*2 *Infection Diagnosis*," J. Med. Virol. doi: 10.1002/jmv.25727) teaches that a point-of-care lateral flow immunoassay could be used to simultaneously detect anti-SARS-CoV-2 IgM and IgG antibodies in human blood and thus avoid the problems of the RdRp-P2 assay of Corman, V. M. et al. Immunoassays, however, may fail to discriminate between individuals suffering from COVID-19 and individuals who were previously infected with SARS-CoV-2, but have since recovered.

In sum, despite all prior efforts a need remains for a method of rapidly and accurately assaying for the presence of SARS-CoV-2. The present invention is directed to this and other goals.

SUMMARY OF THE INVENTION

The present invention is directed to methods for assaying for the presence of SARS-CoV-2 in a sample, including a clinical sample, and to oligonucleotides, reagents and kits useful in such assays. In particular, the present invention is directed to such assays that are rapid, accurate and specific for the detection of SARS-CoV-2.

In detail, the invention provides an oligonucleotide, having a 5' terminus and a 3' terminus, wherein the oligonucleotide has a nucleotide sequence that consists essentially of the nucleotide sequence that consists of, consists essentially of, or is a variant of, the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:12

The invention additionally provides an oligonucleotide, having a 5' terminus and a 3' terminus, wherein the oligonucleotide has a nucleotide sequence that consists of the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:12.

The invention additionally provides the above-described oligonucleotide wherein the oligonucleotide has a nucleotide sequence that consists of the nucleotide sequence of SEQ ID NO: 1.

The invention additionally provides the above-described oligonucleotide wherein the oligonucleotide has a nucleotide sequence that consists of the nucleotide sequence of SEQ ID NO:2.

The invention additionally provides the above-described oligonucleotide wherein the oligonucleotide has a nucleotide sequence that consists of the nucleotide sequence of SEQ ID NO:3.

The invention additionally provides the above-described oligonucleotide wherein the oligonucleotide has a nucleotide sequence that consists of the nucleotide sequence of SEQ ID NO:4.

The invention additionally provides the above-described oligonucleotide wherein the oligonucleotide has a nucleotide sequence that consists of the nucleotide sequence of SEQ ID NO:5.

The invention additionally provides the above-described oligonucleotide wherein the oligonucleotide has a nucleotide sequence that consists of the nucleotide sequence of SEQ ID NO:6.

The invention additionally provides the above-described oligonucleotide wherein the oligonucleotide has a nucleotide sequence that consists of the nucleotide sequence of SEQ ID NO:7.

The invention additionally provides the above-described oligonucleotide wherein the oligonucleotide has a nucleotide sequence that consists of the nucleotide sequence of SEQ ID NO:8.

The invention additionally provides the above-described oligonucleotide wherein the oligonucleotide has a nucleotide sequence that consists of the nucleotide sequence of SEQ ID NO:9.

The invention additionally provides the above-described oligonucleotide wherein the oligonucleotide has a nucleotide sequence that consists of the nucleotide sequence of SEQ ID NO:10.

The invention additionally provides the above-described oligonucleotide wherein the oligonucleotide has a nucleotide sequence that consists of the nucleotide sequence of SEQ ID NO:11.

The invention additionally provides the above-described oligonucleotide wherein the oligonucleotide has a nucleotide sequence that consists of the nucleotide sequence of SEQ ID NO:12.

The invention additionally provides the above-described oligonucleotide wherein the oligonucleotide has a nucleotide sequence that consists of the nucleotide sequence of SEQ ID NO:9, or the nucleotide sequence of SEQ ID NO:10, wherein the oligonucleotide has a 5' terminus that is labeled with a fluorophore and a 3' terminus that is complexed to a quencher of fluorescence of the fluorophore.

The invention additionally provides the above-described oligonucleotide wherein the oligonucleotide has a nucleotide sequence that consists of the nucleotide sequence of SEQ ID NO:11, or the nucleotide sequence of SEQ ID NO:12, wherein the oligonucleotide has a 5' terminus that is labeled with a fluorophore and a 3' terminus that is complexed to a quencher of fluorescence of the fluorophore.

The invention additionally provides the embodiment of the above-described oligonucleotides, wherein the fluorophore has an excitation wavelength within the range of about 352-690 nm and an emission wavelength within the range of about 447-705 nm.

The invention additionally provides the embodiment of such above-described oligonucleotides, wherein the fluorophore is JOE or FAM.

The invention additionally provides a method for detecting the presence of SARS-CoV-2 in a clinical sample, wherein the method comprises:

(I) incubating the clinical sample in vitro in the presence of:

(1) a reverse transcriptase and a DNA polymerase having a 5'→3' exonuclease activity; and (2) a Forward ORF1ab Primer having a nucleotide sequence that consists of, consists essentially of, or is a variant of, the nucleotide sequence of SEQ ID NO:1;

(3) a Reverse ORF1ab Primer having a nucleotide sequence that consists of, consists essentially of, or is a variant of, the nucleotide sequence of SEQ ID NO:2;

(4) an ORF1ab Probe, the ORF1ab Probe being an oligonucleotide having a nucleotide sequence that consists of, consists essentially of, or is a variant of, the nucleotide sequence of SEQ ID NO:9 or SEQ ID NO:10, wherein the ORF1ab Probe oligonucleotide has a 5' terminus that is labeled with a fluorophore and a 3' terminus that is complexed to a quencher of fluorescence of the fluorophore; and wherein the incubation is in a reaction under conditions sufficient to permit:

(a) the Forward and Reverse ORF1ab Primers to mediate a polymerase chain reaction amplification of a region of the ORF1ab of SARS-CoV-2 to thereby produce amplified ORF1ab oligonucleotide molecules, if the SARS-CoV-2 is present in the clinical sample;

(b) the ORF1ab Probe to hybridize to amplified ORF1ab oligonucleotide molecules;

(c) the 5'→3' exonuclease activity to hydrolyze hybridized ORF1ab Probe, to thereby separate the fluorophore thereof from the quencher thereof and cause a fluorescent signal to become detectable; and (II) determining whether the SARS-CoV-2 is present in the clinical sample by determining whether a fluorescent signal of the fluorophore has become detectable.

The invention additionally provides the embodiment of the above-described method, wherein the fluorophore has an excitation wavelength within the range of about 352-690 nm and an emission wavelength within the range of about 447-705 nm.

The invention additionally provides the embodiment of the above-described method, wherein the fluorophore is JOE or FAM.

The invention additionally provides a method for detecting the presence of SARS-CoV-2 in a clinical sample, wherein the method comprises:

(I) incubating the clinical sample in vitro in the presence of:

(1) a reverse transcriptase and a DNA polymerase having a 5'-3' exonuclease activity; and (2) a Forward S Gene Primer having a nucleotide sequence that consists of, consists essentially of, or is a variant of, the nucleotide sequence of SEQ ID NO:5;

(3) a Reverse S Gene Primer having a nucleotide sequence that consists of, consists essentially of, or is a variant of, the nucleotide sequence of SEQ ID NO:6;

(4) an S Gene Probe, the S Gene Probe being an oligonucleotide having a nucleotide sequence that consists of, consists essentially of, or is a variant of, the nucleotide sequence of SEQ ID NO:11 or SEQ ID NO:12, wherein the S Gene Probe oligonucleotide has a 5' terminus that is labeled with a fluorophore and a 3' terminus that is complexed to a quencher of fluorescence of the fluorophore; and wherein the incubation is in a reaction under conditions sufficient to permit:

(a) the Forward and Reverse S Gene Primers to mediate a polymerase chain reaction amplification of a region of the S gene of SARS-CoV-2 to thereby produce amplified S gene oligonucleotide molecules, if the SARS-CoV-2 is present in the clinical sample;

(b) the S Gene Probe to hybridize to amplified S gene oligonucleotide molecules;

(c) the 5'→3' exonuclease activity to hydrolyze hybridized S Gene Probe, to thereby separate the fluorophore thereof from the quencher thereof and cause a fluorescent signal to become detectable; and (II) determining whether the SARS-CoV-2 is present in the clinical sample by determining whether a fluorescent signal of the fluorophore has become detectable.

The invention additionally provides the embodiment of the above-described method, wherein the fluorophore has an excitation wavelength within the range of about 352-690 nm and an emission wavelength within the range of about 447-705 nm.

The invention additionally provides the embodiment of the above-described oligonucleotides, wherein the fluorophore is JOE or FAM.

The invention additionally provides a method for detecting the presence of SARS-CoV-2 in a clinical sample, wherein the method comprises:

(I) incubating the clinical sample in vitro in the presence of:

(1) a reverse transcriptase and a DNA polymerase having a 5'→3' exonuclease activity; and (2) a Forward S Gene Primer having a nucleotide sequence that consists of, consists essentially of, or is a variant of, the nucleotide sequence of SEQ ID NO:5;

(3) a Reverse S Gene Primer having a nucleotide sequence that consists of, consists essentially of, or is a variant of, the nucleotide sequence of SEQ ID NO:6;

(4) an S Gene Probe, the S Gene Probe being an oligonucleotide having a nucleotide sequence that consists of, consists essentially of, or is a variant of, the nucleotide sequence of SEQ ID NO:11 or SEQ ID NO:12, wherein the S Gene Probe oligonucleotide has a 5' terminus that is labeled with a fluorophore and a 3' terminus that is complexed to a quencher of fluorescence of the fluorophore; and (5) a Forward ORF1ab Primer having a nucleotide sequence that consists of, consists essentially of, or is a variant of, the nucleotide sequence of SEQ ID NO:1;

(6) a Reverse ORF1ab Primer having a nucleotide sequence that consists of, consists essentially of, or is a variant of, the nucleotide sequence of SEQ ID NO:2;

(7) an ORF1ab Probe, the ORF1ab Probe being an oligonucleotide having a nucleotide sequence that consists of, consists essentially of, or is a variant of, the nucleotide sequence of SEQ ID NO:9 or SEQ ID NO:10, wherein the ORF1ab Probe oligonucleotide has a 5' terminus that is labeled with a fluorophore and a 3' terminus that is complexed to a quencher of fluorescence of the fluorophore; wherein the fluorescence of the fluorophore of the ORF1ab Probe is distinguishable from the fluorescence of the fluorophore of the S Gene Probe; and wherein the incubation is in a reaction under conditions sufficient to permit:

(a) the Forward and Reverse S Gene Primers to mediate a polymerase chain reaction amplification of a region of the S gene of SARS-CoV-2 to thereby produce amplified S gene oligonucleotide molecules, if the SARS-CoV-2 is present in the clinical sample;

(b) the S Gene Probe to hybridize to amplified S gene oligonucleotide molecules;

(c) the 5'→3' exonuclease activity to hydrolyze hybridized S Gene Probe, to thereby separate the fluorophore thereof from the quencher thereof and cause a fluorescent signal to become detectable; and (II) determining whether the SARS-CoV-2 is present in the clinical sample by determining whether a fluorescent signal of the fluorophore has become detectable.

The invention additionally provides the embodiments of such methods, wherein the fluorophore of the ORF1ab Probe and the fluorophore of the S Gene Probe have an excitation wavelength within the range of about 352-690 nm and an emission wavelength within the range of about 447-705 nm.

The invention additionally provides the embodiments of such methods, wherein one of the fluorophores of the ORF1ab Probe and the S Gene Probe is JOE and the other of such fluorophores is FAM.

The invention additionally provides a kit for detecting the presence of SARS-CoV-2 in a clinical sample, wherein the kit comprises:

(I) a container containing a reagent, wherein the reagent comprises:

(1) a Forward ORF1ab Primer having a nucleotide sequence that consists of, consists essentially of, or is a variant of, the nucleotide sequence of SEQ ID NO:1;

(2) a Reverse ORF1ab Primer having a nucleotide sequence that consists of, consists essentially of, or is a variant of, the nucleotide sequence of SEQ ID NO:2;

(3) an ORF1ab Probe, the ORF1ab Probe being an oligonucleotide having a nucleotide sequence that consists of, consists essentially of, or is a variant of the nucleotide sequence of SEQ ID NO:9 or SEQ ID NO:10, wherein the ORF1ab Probe oligonucleotide has a 5' terminus that is labeled with a fluorophore and a 3' terminus that is complexed to a quencher of fluorescence of the fluorophore; and (II) instructions for using such reagent to detect the presence of SARS-CoV-2 in the clinical sample.

The invention additionally provides the embodiments of such kit, wherein the fluorophore of the ORF1ab Probe has an excitation wavelength within the range of about 352-690 nm and an emission wavelength within the range of about 447-705 nm.

The invention additionally provides the embodiments of such kit, wherein the fluorophore of the ORF1 ab Probe is JOE or FAM.

The invention additionally provides a kit for detecting the presence of SARS-CoV-2 in a clinical sample, wherein the kit comprises:

(I) a container containing a reagent, wherein the reagent comprises:

(1) a Forward S Gene Primer having a nucleotide sequence that consists of, consists essentially of, or is a variant of, the nucleotide sequence of SEQ ID NO:5;

(2) a Reverse S Gene Primer having a nucleotide sequence that consists of, consists essentially of, or is a variant of, the nucleotide sequence of SEQ ID NO:6;

(3) an S Gene Probe, the S Gene Probe being an oligonucleotide having a nucleotide sequence that consists of, consists essentially of, or is a variant of, the nucleotide sequence of SEQ ID NO:11 or SEQ ID NO:12, wherein the S Gene Probe oligonucleotide has a 5' terminus that is labeled with a fluorophore and a 3' terminus that is complexed to a quencher of fluorescence of the fluorophore; and (II) instructions for using such reagent to detect the presence of SARS-CoV-2 in the clinical sample.

The invention additionally provides the embodiments of such kit, wherein the fluorophore of the S Gene Probe has an excitation wavelength within the range of about 352-690 nm and an emission wavelength within the range of about 447-705 nm.

The invention additionally provides the embodiments of such kit, wherein the fluorophore of the S Gene Probe is JOE or FAM.

The invention additionally provides a kit for detecting the presence of SARS-CoV-2 in a clinical sample, wherein the kit comprises:

(I) reagents for detecting SARS-CoV-2 ORF1ab, wherein the SARS-CoV-2 ORF1ab detection reagents comprise:

(1) a Forward ORF1ab Primer having a nucleotide sequence that consists of, consists essentially of, or is a variant of, the nucleotide sequence of SEQ ID NO:1;

(2) a Reverse ORF1ab Primer having a nucleotide sequence that consists of, consists essentially of, or is a variant of, the nucleotide sequence of SEQ ID NO:2; and (3) an ORF1ab Probe, the ORF1ab Probe being an oligonucleotide having a nucleotide sequence that consists of, consists essentially of, or is a variant of, the nucleotide sequence of SEQ ID NO:9 or SEQ ID NO:10, wherein the ORF1ab Probe oligonucleotide has a 5' terminus that is labeled with a fluorophore and a 3' terminus that is complexed to a quencher of fluorescence of the fluorophore; and (II) instructions for using such detection reagents to detect the presence of SARS-CoV-2 in the clinical sample.

The invention provides the embodiment of such kit wherein the fluorophore of the ORF1ab Probe has an excitation wavelength within the range of about 352-690 nm and an emission wavelength within the range of about 447-705 nm. The invention also provides the embodiment of such kit wherein the fluorophore of the ORF1ab is JOE or FAM.

The invention additionally provides a kit for detecting the presence of SARS-CoV-2 in a clinical sample, wherein the kit comprises:

(I) reagents for detecting SARS-CoV-2 S gene, wherein the SARS-CoV-2 S gene detection reagents comprise:

(1) a Forward S Gene Primer having a nucleotide sequence that consists of, consists essentially of, or is a variant of, the nucleotide sequence of SEQ ID NO:5;

(2) a Reverse S Gene Primer having a nucleotide sequence that consists of, consists essentially of, or is a variant of, the nucleotide sequence of SEQ ID NO:6; and (3) an S Gene Probe, the S Gene Probe being an oligonucleotide having a nucleotide sequence that consists of, consists essentially of, or is a variant of, the nucleotide sequence of SEQ ID NO:11 or SEQ ID NO:12, wherein the S Gene Probe oligonucleotide has a 5' terminus that is labeled with a fluorophore and a 3' terminus that is complexed to a quencher of fluorescence of the fluorophore; and (II) instructions for using such detection reagents to detect the presence of SARS-CoV-2 in the clinical sample.

The invention provides the embodiment of such kit wherein the fluorophore of the S Gene Probe has an excitation wavelength within the range of about 352-690 nm and an emission wavelength within the range of about 447-705 nm. The invention also provides the embodiment of such kit wherein the fluorophore of the ORF1ab is JOE or FAM.

The invention additionally provides a kit for detecting the presence of SARS-CoV-2 in a clinical sample, wherein the kit comprises:

(I) (A) reagents for detecting SARS-CoV-2 ORF1ab, wherein the SARS-CoV-2 ORF1ab detection reagents comprise:

(1) a Forward ORF1ab Primer having a nucleotide sequence that consists of, consists essentially of, or is a variant of, the nucleotide sequence of SEQ ID NO:1;

(2) a Reverse ORF1ab Primer having a nucleotide sequence that consists of, consists essentially of, or is a variant of, the nucleotide sequence of SEQ ID NO:2; and (3) an ORF1ab Probe, the ORF1ab Probe being an oligonucleotide having a nucleotide sequence that consists of, consists essentially of, or is a variant of, the nucleotide sequence of SEQ ID NO:9 or SEQ ID NO:10, wherein the ORF1ab Probe oligonucleotide has a 5' terminus that is labeled with a fluorophore and a 3' terminus that is complexed to a quencher of fluorescence of the fluorophore; and (B) reagents for detecting SARS-CoV-2 S gene, wherein the SARS-CoV-2 S gene detection reagents comprise:

(1) a Forward S Gene Primer having a nucleotide sequence that consists of, consists essentially of, or is a variant of, the nucleotide sequence of SEQ ID NO:5;

(2) a Reverse S Gene Primer having a nucleotide sequence that consists of, consists essentially of, or is a variant of, the nucleotide sequence of SEQ ID NO:6; and (3) an S Gene Probe, the S Gene Probe being an oligonucleotide having a nucleotide sequence that consists of, consists essentially of, or is a variant of, the nucleotide sequence of SEQ ID NO:11 or SEQ ID NO:12, wherein the S Gene Probe oligonucleotide has a 5' terminus that is labeled with a fluorophore and a 3' terminus that is complexed to a quencher of fluorescence of the fluorophore; wherein the fluorescence of the fluorophore of the S Gene Probe is distinguishable from the fluorescence of the fluorophore of the ORF1ab Probe; and (II) instructions for using such reagent to detect the presence of SARS-CoV-2 in the clinical sample.

The invention additionally provides the embodiments of such kits wherein the fluorophore of the ORF1ab Probe and the fluorophore of the S Gene Probe have an excitation wavelength within the range of about 352-690 nm and an emission wavelength within the range of about 447-705 nm.

The invention additionally provides the embodiments of such kits wherein one of the fluorophores of the ORF1ab Probe and the S Gene Probe is JOE and the other of such fluorophores is FAM.

DETAILED DESCRIPTION OF THE INVENTION

Figure 1:
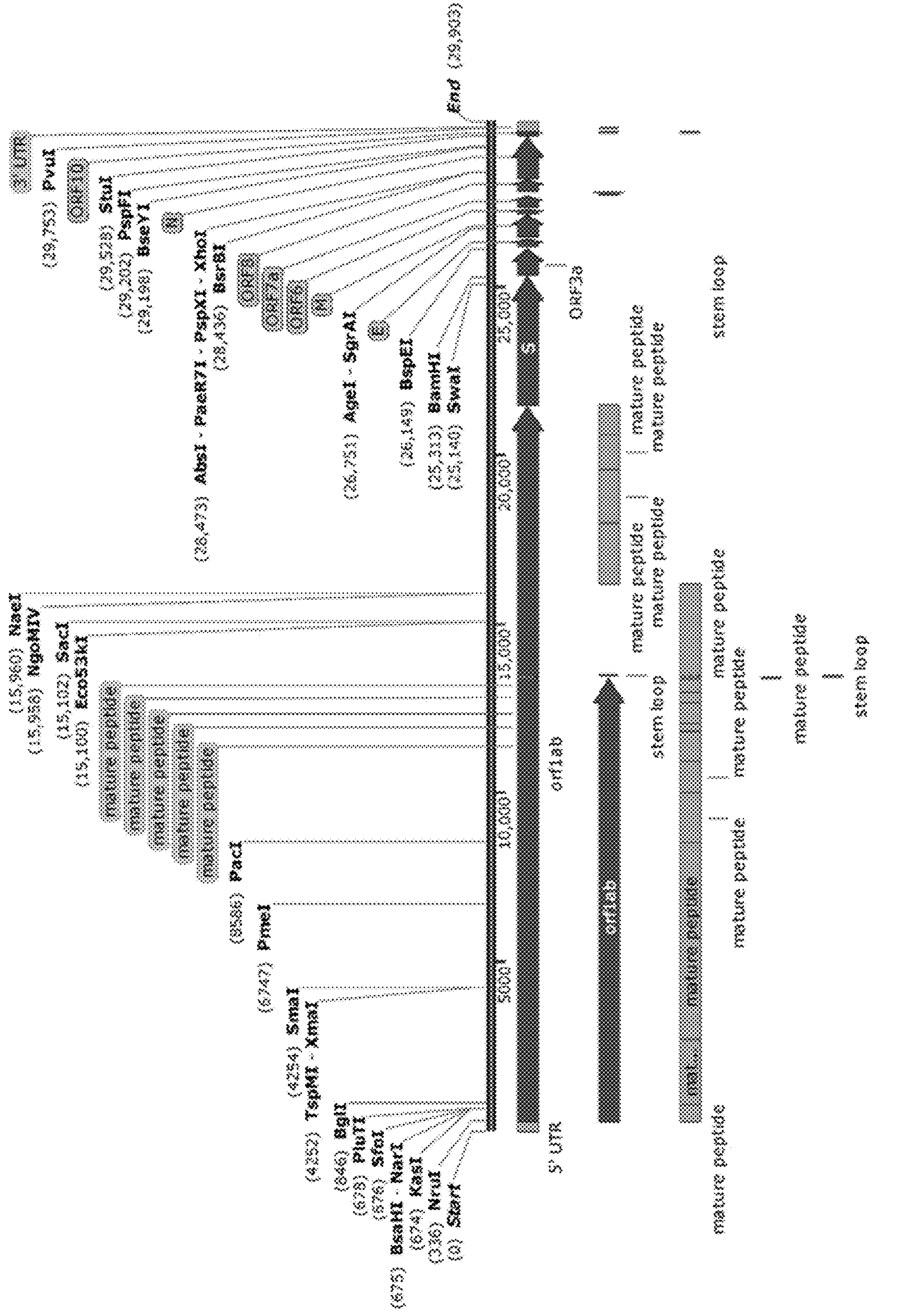
FIG. 1 provides an illustration of the structure of SARS-CoV-2 and its open reading frames (ORFs). The sequence presented is that of the reference SARS-CoV-2 sequence (GenBank NC 045512).

The present invention is directed to methods for assaying for the presence of SARS-CoV-2 in a sample, including a clinical sample, and to oligonucleotides, reagents and kits useful in such assays. In particular, the present invention is directed to such assays that are rapid, accurate and specific for the detection of SARS-CoV-2.

As used herein, an assay for the detection of SARS-CoV-2 is said to be "specific" for SARS-CoV-2 if it can be conducted under conditions that permit it to detect SARS-CoV-2 without exhibiting cross-reactivity to human DNA, or to DNA (or cDNA) of other pathogens, especially other coronavirus pathogens. In particular, an assay for the detection of SARS-CoV-2 is said to be specific for SARS-CoV-2 if it can be conducted under conditions that permit it to detect SARS-CoV-2 without exhibiting cross-reactivity to DNA (or cDNA) of Influenza A, Influenza B, Respiratory Syncytial Virus, Group A *Streptococcus* (*Streptococcus pyogenes*), Parainfluenza I, Parainfluenza III, *Haemophilus parainfluenzae*, Enterovirus or Adenovirus, or to SARS-CoV, MERS-CoV, or bat-derived Severe Acute Respiratory Syndrome-like coronaviruses, such as bat-SL-CoVZC45 or bat-SL-CoVZXC21. More preferably, an assay for the detection of SARS-CoV-2 is said to be specific for SARS-CoV-2 if it can be conducted under conditions that permit it to detect SARS-CoV-2 without exhibiting cross-reactivity to DNA (or cDNA) of Adenovirus 1, *Bordetella pertussis, Chlamydophila pneumoniae*, Coronavirus 229E, Coronavirus NL63, Coronavirus OC43, Enterovirus 68, *Haemophilus influenzae*, Human metapneumovirus (hMPV-9), Influenza A H3N2 (Hong Kong 8/68), Influenza B (Phuket 3073/2013), *Legionella pneumophilia*, MERS-Coronavirus, *Mycobacterium tuberculosis*, Parainfluenza Type 1, Parainfluenza Type 2, Parainfluenza Type 3, Parainfluenza Type 4A, Rhinovirus B14, RSV A Long, RSV B Washington, SARS-Coronavirus, SARS-Coronavirus HKU39849, *Streptococcus pneumoniae, Streptococcus pyogenes*, human leukocytes, or pooled human nasal fluid.

As used herein, an assay for the detection of SARS-CoV-2 is said to be "accurate" for SARS-CoV-2 if it is capable of detecting a viral dose of 400 copies/ml of SARS-CoV-2 with an LoD of at least 80%, and of detecting a viral dose of 500 copies/ml of SARS-CoV-2 with an LoD of at least 90%.

As used herein, an assay for the detection of SARS-CoV-2 is said to be "rapid" for SARS-CoV-2 if it is capable of providing a determination of the presence or absence of SARS-CoV-2 within 2 hours, and more preferably within 90 minutes and most preferably, within 1 hour after the commencement of the assay.

III. Preferred Assays for the Detection of SARS-CoV-2

A. Preferred Assay Formats

The present invention provides an assay for detecting the presence of SARS-CoV-2 in a clinical sample. Such detection may be accomplished in situ or in vitro, but is preferably conducted in vitro. The clinical samples that may be evaluated include any that may contain SARS-CoV-2, and include blood samples, bronchoalveolar lavage fluid specimens, fecal samples, fibrobronchoscope brush biopsy samples, nasal swab samples, nasopharyngeal swab samples, pharyngeal swab sample, sputum samples and urine samples. Preferably, however, the employed clinical sample will be a nasal swab sample, a nasopharyngeal swab sample, a pharyngeal swab sample, or a sputum sample, and most preferably, the employed clinical sample will be a nasopharyngeal swab sample. In one embodiment, the sample will be pre-treated to extract RNA that may be present in the sample. Alternatively, and more preferably, the sample will be evaluated without prior RNA extraction.

The present invention preferably uses a real-time reverse transcriptase polymerase chain reaction (rRT-PCR) assay to detect the presence of SARS-CoV-2 in clinical samples. rRT-PCR assays are well known and widely deployed in diagnostic virology (see, e.g., Pang, J. et al. (2020) "*Potential Rapid Diagnostics, Vaccine and Therapeutics for* 2019 *Novel Coronavirus* (2019-*nCoV*): *A Systematic Review*," J. Clin. Med. 26; 9(3)E623 doi: 10.3390/jcm9030623; Kralik, P. et al. (2017) "*A Basic Guide to Real-Time PCR in Microbial Diagnostics: Definitions, Parameters, and Everything*," Front. Microbiol. 8:108. doi: 10.3389/fmicb.2017.00108).

To more easily describe the rRT-PCR assays of the present invention, such assays may be envisioned as involving multiple reaction steps:

(1) the reverse transcription of SARS-CoV-2 RNA that may be present in the clinical sample that is to be evaluated for SARS-CoV-2 presence;

(2) the PCR-mediated amplification of the SARS-CoV-2 cDNA produced from such reverse transcription;

(3) the hybridization of SARS-CoV-2-specific probes to such amplification products;

(4) the double-strand-dependent 5"→3" exonuclease cleavage of the hybridized SARS-CoV-2-specific probes; and (5) the detection of the unquenched probe fluorophores signifying that the evaluated clinical sample contained SARS-CoV-2.

It will be understood that such steps may be conducted separately (for example, in two or more reaction chambers, or with reagents for the different steps being added at differing times, etc.). However, it is preferred that such steps are to be conducted within the same reaction chamber, and that all reagents needed for the rRT-PCR assays of the present invention are to be provided to the reaction chamber at the start of the assay. It will also be understood that although the polymerase chain reaction (PCR) (see, e.g. Ghannam, M. G. et al. (2020) "*Biochemistry, Polymerase Chain Reaction* (*PCR*)," StatPearls Publishing, Treasure Is.; pp 0.1-4; Lorenz, T. C. (2012) "*Polymerase Chain Reaction: Basic Protocol Plus Troubleshooting And Optimization Strategies*," J. Vis. Exp. 2012 May 22; (63):e3998; pp. 1-15) is the preferred method of amplifying SARS-CoV-2 cDNA produced via reverse transcription, other DNA amplification technologies could alternatively be employed.

Accordingly, in a preferred embodiment, the rRT-PCR assays of the present invention comprise incubating a clinical sample in the presence of a DNA polymerase, a reverse transcriptase, one or more pairs of SARS-CoV-2-specific primers, one or more SARS-CoV-2-specific probes (typically, at least one probe for each region being amplified by an employed pair of primers), deoxynucleotide triphosphates (dNTPs) and buffers. The conditions of the incubation are cycled to permit the reverse transcription of SARS-CoV-2 RNA, the amplification of SARS-CoV-2 cDNA, the hybridization of SARS-CoV-2-specific probes to such cDNA, the cleavage of the hybridized SARS-CoV-2-specific probes and the detection of unquenched probe fluorophores.

The rRT-PCR assays of the present invention employs at least one set of at least one "Forward" primer that hybridizes to a polynucleotide portion of a first strand of a DNA molecule, and at least one "Reverse" primer that hybridizes to a polynucleotide portion of a second (and complementary) strand of such DNA molecule.

Preferably, such Forward and Reverse primers will permit the amplification of a region of ORF1ab, which encodes a non-structural polyprotein of SARS-CoV-2 and/or a region of the S gene, which encodes the virus spike surface glycoprotein and is required for host cell targeting; the SARS-CoV-2 spike surface glycoprotein is a key protein for specifically characterizing a coronavirus as being SARS-CoV-2 (Chen, Y. et al. (2020) "*Structure Analysis Of The Receptor Binding Of* 2019-*Ncov*," Biochem. Biophys. Res. Commun. 525:135-140; Masters, P. S. (2006) "*The Molecular Biology Of Coronaviruses*," Adv. Virus Res. 66:193-292). The amplification of either of such targets alone is sufficient for the specific determination of SARS-CoV-2 presence in clinical samples. It is, however, preferred to assay for SARS-CoV-2 by amplifying both such targets.

The presence of such amplified molecules is preferably detected using probes that are capable of hybridizing to a oligonucleotide region present within the oligonucleotide that is amplified by the above-described SARS-CoV-2-specific primers. Such detection can be accomplished using any suitable method, e.g., molecular beacon probes, scorpion primer-probes, TaqMan probes, etc. (Navarro, E. et al. (2015) "*Real-Time PCR Detection Chemistry*," Clin. Chim. Acta 439:231-250). All of these methods employ an oligonucleotide that is labeled with a fluorophore and complexed to a quencher of the fluorescence of that fluorophore.

A wide variety of fluorophores and quenchers are known and are commercially available (e.g., Biosearch Technologies, Gene Link), and may be used in accordance with the methods of the present invention. Preferred fluorophores include the fluorophores Biosearch Blue, Alexa488, FAM, Oregon Green, Rhodamine Green-X, NBD-X, TET, Alexa430, BODIPY R6G-X, CAL Fluor Gold 540, JOE, Yakima Yellow, Alexa 532, VIC, HEX, and CAL Fluor Orange 560 (which have an excitation wavelength in the range of about 352-538 nm and an emission wavelength in the range of about 447-559 nm, and whose fluorescence can be quenched with the quencher BHQ1), or the fluorophores RBG, Alexa555, BODIPY 564/570, BODIPY TMR-X, Quasar 570, Cy3, Alexa 546, NED, TAMRA, Rhodamine Red-X, BODIPY 581/591, Redmond Red, CAL Fluor Red 590, Cy3.5, ROX, Alexa 568, CAL Fluor Red 610, BODIPY TR-X, Texas Red, CAL Fluor Red 635, Pulsar 650, Cy5, Quasar 670, CY5.5, Alexa 594, BODIPY 630/650-X, or Quasar 705 (which have an excitation wavelength in the range of about 524-690 nm and an emission wavelength in the range of about 557-705 nm, and whose fluorescence can be quenched with the quencher BHQ2). The preferred SARS-CoV-2-specific TaqMan probes of the present invention are labeled with either the fluorophore 2',7'-dimethoxy-4',5'-dichloro-6-carboxyfluorescein ("JOE") or the fluorophore 5(6)-carboxyfluorescein ("FAM") on their 5' termini. JOE is a xanthene fluorophore with an emission in yellow range (absorption wavelength of 520 nm; emission wavelength of 548 nm). FAM is a carboxyfluorescein molecule with an absorption wavelength of 495 nm and an emission wavelength of 517 nm; it is typically provided as a mixture of two isomers (5-FAM and 6-FAM). Quasar 670 is similar to cyanine dyes, and has an absorption wavelength of 647 nm and an emission wavelength of 670 nm.

The black hole quencher 1 ("BHQ1") is a preferred quencher for FAM and JOE fluorophores. BHQ1 quenches fluorescent signals of 480-580 nm and has an absorption maximum at 534 nm.

The black hole quencher 2 ("BHQ2") is a preferred quencher for Quasar 670. BHQ2 quenches fluorescent signals of 560-670 nm and has an absorption maximum at 579 nm.

JOE, FAM, Quasar 670, BHQ1 and BHQ2 are widely available commercially (e.g., Sigma Aldrich; Biosearch Technologies, etc.) and are coupled to oligonucleotides using methods that are well known (see, e.g., Zearfoss, N. R. et al. (2012) "*End-Labeling Oligonucleotides with Chemical Tags After Synthesis*," Meth. Mol. Biol. 941:181-193). Oligonucleotide probes of any desired sequence labeled may be obtained commercially (e.g., ThermoFisher Scientific) already labeled with a desired fluorophore and complexed with a desired quencher.

As discussed above, the proximity of the quencher of a TaqMan probe to the fluorophore of the probe results in a quenching of the fluorescent signal. Incubation of the probe in the presence of a double-strand-dependent 5'→3' exonuclease (such as the 5"→3" exonuclease activity of Taq polymerase) cleaves the probe when it has hybridized to a complementary target sequence, thus separating the fluorophore from the quencher and permitting the production of a detectable fluorescent signal. The chemistry and design of "TaqMan" probes is reviewed by Holland, P. M. et al. (1991) ("*Detection Of Specific Polymerase Chain Reaction Product By Utilizing The 5'→3' Exonuclease Activity Of Thermus Aquaticus DNA Polymerase*," Proc. Natl. Acad. Sci. (U.S.A.) 88(16):7276-7280), by Navarro, E. et al. (2015) ("*Real-Time PCR Detection Chemistry*," Clin. Chim. Acta 439:231-250), and by Gasparic, B. M. et al. (2010) ("*Comparison Of Nine Different Real-Time PCR Chemistries For Qualitative And Quantitative Applications In GMO Detection*," Anal. Bioanal. Chem. 396(6):2023-2029).

Molecular beacon probes can alternatively be employed to detect amplified SARS-CoV-2 oligonucleotides in accordance with the present invention. Molecular beacon probes are also labeled with a fluorophore and complexed to a quencher. However, in such probes, the quenching of the fluorescence of the fluorophore only occurs when the quencher is directly adjacent to the fluorophore. Molecular beacon probes are thus designed to adopt a hairpin structure while free in solution (thus bringing the fluorescent dye and quencher into close proximity with one another). When a molecular beacon probe hybridizes to a target, the fluorophore is separated from the quencher, and the fluorescence of the fluorophore becomes detectable. Unlike TaqMan probes, molecular beacon probes are designed to remain intact during the amplification reaction, and must rebind to target in every cycle for signal measurement. The chemistry and design of molecular beacon probes is reviewed by Han, S. X. et al. (2013) ("*Molecular Beacons: A Novel Optical Diagnostic Tool*," Arch. Immunol. Ther. Exp. (Warsz). 61(2):139-148), by Navarro, E. et al. (2015) ("*Real-Time PCR Detection Chemistry*," Clin. Chim. Acta 439:231-250), by Goel, G. et al. (2005) ("*Molecular Beacon: A Multitask Probe*," J. Appl. Microbiol. 99(3):435-442) and by Zheng, J. et al. (2015) ("*Rationally Designed Molecular Beacons For Bioanalytical And Biomedical Applications*," Chem. Soc. Rev. 44(10):3036-3055).

Scorpion primer-probes (Whitcombe, D. et al. (1999) "*Detection Of PCR Products Using Self-Probing Amplicons And Fluorescence*," Nat. Biotechnol. 17(8):804-807) can alternatively be employed to detect amplified SARS-CoV-2 oligonucleotides in accordance with the present invention. Scorpion primer-probes are also designed to adopt a hairpin structure while free in solution, and are also labeled with a fluorophore at their 5' terminus and complexed to a quencher at their 3' terminus. Scorpion primer-probes differ from molecular beacon probes in that their 3'-end is attached to their 5'-end by a hexathylene glycol (HEG) blocker. Such attachment prevents the polymerase-mediated extension of the 3' terminus of the scorpion primer-probe. However, after the scorpion primer-probe has bound to its target DNA, the polymerase copies the sequence of nucleotides from its 3'-end. In the next denaturation step, the specific sequence of the scorpion primer-probe binds to the complementary region within the same strand of newly amplified DNA. This hybridization opens the hairpin structure and, as a result, separates the molecules fluorophore from its quencher and permits fluorescence to be detected.

In a preferred embodiment, the probes of the present invention are TaqMan probes. As described above, such probes are labeled on their 5' termini with a fluorophore, and are complexed on their 3' termini with a quencher of the fluorescence of that fluorophore. In order to simultaneously detect the amplification of two polynucleotide portions of SARS-CoV-2, two TaqMan probes are employed that have different fluorophores (with differing and distinguishable emission wavelengths); the employed quenchers may be the same or different. In one embodiment of the invention, the 5' terminus of the ORF1ab Probe is labeled with the fluorophore JOE, and the 3' terminus of such probe is complexed to the quencher BHQ1 and the 5' terminus of the S Gene Probe is labeled with the fluorophore FAM, and the 3' terminus of such probe is complexed to the quencher BHQ1. In an alternative embodiment, the 5' terminus of the ORF1ab Probe is labeled with the fluorophore FAM, and the 5' terminus of the S Gene Probe is labeled with the fluorophore JOE. The use of such two fluorophores permits both probes to be used in the same assay.

The preferred primers and probes described below were designed for the specific detection of SARS-CoV-2. Each target on its own has been shown to provide sensitive and specific detection of SARS-CoV-2 with no detection of, or cross-reactivity to, other coronaviruses. The invention includes oligonucleotides whose nucleotide sequences consist of, consist essentially of, or are "variants" of such preferred primers and probes. As used herein, an oligonucleotide is a "variant" of another oligonucleotide if it retains the function of such oligonucleotide (e.g., acting as a specific primer or probe), but:

(1) lacks 1, 2, 3, 4, 5, 6, 7, 8, 9, or 10 nucleotides of the nucleotides of such primer or probe, or
(2) lacks 1, 2, 3, 4, 5, 6, 7, 8, 9, or 10 of the 10 3' terminal nucleotides of such primer or probe, or
(3) lacks 1, 2, 3, 4, 5, 6, 7, 8, 9, or 10 of the 10 5' terminal nucleotides of such primer or probe, or
(4) has a sequence that differs from that of such primer or probe in having 1, 2, 3, 4, 5, 6, 7, 8, 9, 10 or more than 10 additional nucleotides, or
(5) has a sequence that differs from that of such primer or probe in having 1, 2, 3, 4, 5, 6, 7, 8, 9, 10 or more than 10 substitution nucleotides in lieu of the nucleotides present in such primer or probe, or
(6) possesses a combination of such (1)-(5).

B. Preferred SARS-CoV-2-Specific Primers

1. Preferred ORF1ab Primers

The first set of primers comprise a "Forward ORF1ab Primer" and a "Reverse ORF1ab Primer," whose sequences are suitable for amplifying a region of the SARS-CoV-2 ORF1ab. Although any Forward and Reverse ORF1ab Primers capable of mediating such amplification may be employed in accordance with the present invention, it is preferred to employ Forward and Reverse ORF1ab Primers that possess distinctive advantages. The preferred Forward ORF1ab Primer of the present invention comprises, consists essentially of, or consists of, the sequence (SEQ ID NO:1) atggtagagttgatggtcaa, which corresponds to the ORF1ab nucleotide sequence of nucleotides 19991-20010 of the sense strand of SARS-CoV-2. The preferred Reverse ORF1ab Primer of the present invention comprises, consists essentially of, or consists of, the sequence (SEQ ID NO:2) taagactagcttgtttggga, which corresponds to the ORF1ab nucleotide sequence of nucleotides 20088-20107 of the anti-sense strand of SARS-CoV-2. Accordingly, these primers amplify a double-stranded ORF1ab polynucleotide having the sequence of nucleotides 19991-20107 of SARS-CoV-2. Such preferred "Forward ORF1ab Primer" and preferred "Reverse ORF1ab Primer" have distinctive attributes for use in the detection of SARS-CoV-2.

The sequence of the ORF1ab "sense" strand of nucleotides 19991-20107 of the SARS-CoV-2is SEQ ID NO:3; the sequence of the complement ("anti-sense") strand is SEQ ID NO:4:

```
                                           SEQ ID NO: 3
atggtagagt tgatggtcaa gtagacttat ttagaaatgc

ccgtaatggt gttcttatta cagaaggtag tgttaaaggt

ttacaaccat ctgtaggtcc caaacaagct agtctta
```

```
                                           SEQ ID NO: 4
taagactagc ttgtttggga cctacagatg gttgtaaacc

tttaacacta ccttctgtaa taagaacacc attacgggca

tttctaaata agtctacttg accatcaact ctaccat
```

While it is preferred to detect the presence of the ORF1ab using primers that consist of the sequences of SEQ ID NO:1 and SEQ ID NO:2, the invention contemplates that other primers that consist essentially of the sequence of SEQ ID NO:1 or that consist essentially of the sequence of SEQ ID NO:2 (in that they possess 1, 2, 3, 4, 5, 6, 7, 8, 9, or 10 additional nucleotide residues, but retain the ability to specifically hybridize to DNA molecules having the nucleotide sequence of SEQ ID NO:3 or SEQ ID NO:4, and more preferably retain the ability to specifically hybridize to DNA molecules having the nucleotide sequence of complement of the nucleotide sequence of SEQ ID NO:1 or the nucleotide sequence of complement of the nucleotide sequence of SEQ ID NO:2), or "variants" of such primers that retain the ability to specifically hybridize to DNA molecules having the nucleotide sequence of SEQ ID NO:3 or SEQ ID NO:4, and more preferably retain the ability to specifically hybridize to DNA molecules having the nucleotide sequence of complement of the nucleotide sequence of SEQ ID NO:1 or the nucleotide sequence of complement of the nucleotide sequence of SEQ ID NO:2, could be employed in accordance with the principles and goals of the present invention. Such "Variant ORF1ab Primers" may, for example:

(1) lack 1, 2, 3, 4, 5, 6, 7, 8, 9, or 10 nucleotides of SEQ ID NO:1 or of SEQ ID NO:2, or
(2) lack 1, 2, 3, 4, 5, 6, 7, 8, 9, or 10 of the 10 3' terminal nucleotides of the sequence of SEQ ID NO:1 or of SEQ ID NO:2, or
(3) lack 1, 2, 3, 4, 5, 6, 7, 8, 9, or 10 of the 10 5' terminal nucleotides of the sequence of SEQ ID NO:1 or of SEQ ID NO:2, or
(4) have a sequence that differs from that of SEQ ID NO:1 or of SEQ ID NO:2 in having 1, 2, 3, 4, 5, 6, 7, 8, 9, 10 or more than 10 additional nucleotides, or
(5) have a sequence that differs from that of SEQ ID NO:1 or of SEQ ID NO:2 in having 1, 2, 3, 4, 5, 6, 7, 8, 9, 10 or more than 10 substitution nucleotides in lieu of the nucleotides present in SEQ ID NO:1 or of SEQ ID NO:2, or
(6) combinations of such (1)-(5).

Figure 2:
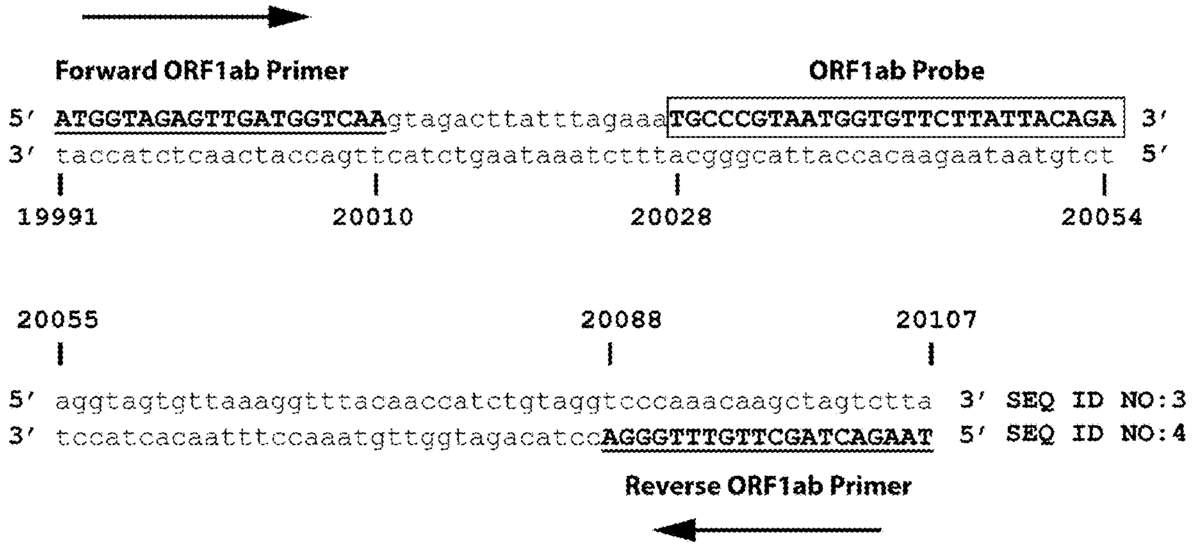
FIG. 2 shows the alignment and orientation of the Forward ORF1ab Primer and Reverse ORF1ab Primer of the present invention and the region of ORF1ab that these primers amplify in an rRT-PCR assay of SARS-CoV-2. Primer sequences are shown in underlined upper case letters; probe sequences are shown in boxed uppercase letters.

The alignment and relative orientation of the preferred Forward ORF1ab Primer (SEQ ID NO:1) and Reverse ORF1ab Primer (SEQ ID NO:2) of the present invention and the region of SARS-CoV-2 ORF1ab that these primers amplify in a rRT-PCR assay of SARS-CoV-2 are shown in FIG. 2.

2. Preferred S Gene Primers

The second set of primers comprise a "Forward S Gene Primer" and a "Reverse S Gene Primer," whose sequences are suitable for amplifying a region of the SARS-CoV-2 S gene. Although any Forward and Reverse S Gene Primers capable of mediating such amplification may be employed in accordance with the present invention, it is preferred to employ Forward and Reverse S Gene Primers that possess distinctive advantages. The preferred Forward S Gene Primer of the present invention comprises, consists essentially of, or consists of, the sequence (SEQ ID NO:5) ctaaccaggttgctgttctt, which corresponds to the S gene nucleotide sequence of nucleotides 23376-23395 of the sense strand of SARS-CoV-2. The preferred Reverse S Gene Primer comprises, consists essentially of, or consists of, the sequence (SEQ ID NO:6) cctgtagaataaacacgcca, which corresponds to the S gene nucleotide sequence of nucleotides 23459-23478 of the anti-sense strand of SARS-CoV-2. Accordingly, these primers amplify a double-stranded S gene polynucleotide having the sequence of nucleotides 23376-23478 of SARS-CoV-2.

The sequence of the S gene "sense" strand of nucleotides 23376-23478 of SARS-CoV-2 is SEQ ID NO:7; the sequence of the complement ("anti-sense") strand is SEQ ID NO:8:

```
                                    SEQ ID NO: 7
ctaaccaggt tgctgttctt tatcaggatg ttaactgcac

agaagtccct gttgctattc atgcagatca acttactcct

acttggcgtg tttattctac agg
```

```
                                    SEQ ID NO: 8
cctgtagaat aaacacgcca agtaggagta agttgatctg

catgaatagc aacagggact tctgtgcagt taacatcctg

ataaagaaca gcaacctggt tag
```

While it is preferred to detect the presence of the S gene using primers that consist of the sequences of SEQ ID NO:5 and SEQ ID NO:6, the invention contemplates that other primers that consist essentially of the sequence of SEQ ID NO:5 or that consist essentially of the sequence of SEQ ID NO:6 (in that they possess 1, 2, 3, 4, 5, 6, 7, 8, 9, or 10 additional nucleotide residues, but retain the ability to specifically hybridize to DNA molecules having the nucleotide sequence of SEQ ID NO:7 or SEQ ID NO:8, and more preferably retain the ability to specifically hybridize to DNA molecules having the nucleotide sequence of complement of the nucleotide sequence of SEQ ID NO:5 or the nucleotide sequence of complement of the nucleotide sequence of SEQ ID NO:6), or "variants" of such primers that retain the ability to specifically hybridize to DNA molecules having the nucleotide sequence of SEQ ID NO:7 or SEQ ID NO:8, and more preferably retain the ability to specifically hybridize to DNA molecules having the nucleotide sequence of complement of the nucleotide sequence of SEQ ID NO:5 or the nucleotide sequence of complement of the nucleotide sequence of SEQ ID NO:6, could be employed in accordance with the principles and goals of the present invention. Such "Variant S Gene Primers" may, for example:

(1) lack 1, 2, 3, 4, 5, 6, 7, 8, 9, or 10 nucleotides of SEQ ID NO:5 or of SEQ ID NO:6, or (2) lack 1, 2, 3, 4, 5, 6, 7, 8, 9, or 10 of the 10 3' terminal nucleotides of the sequence of SEQ ID NO:5 or of SEQ ID NO:6, or (3) lack 1, 2, 3, 4, 5, 6, 7, 8, 9, or 10 of the 10 5' terminal nucleotides of the sequence of SEQ ID NO:5 or of SEQ ID NO:6, or (4) have a sequence that differs from that of SEQ ID NO:5 or of SEQ ID NO:6 in having 1, 2, 3, 4, 5, 6, 7, 8, 9, 10 or more than 10 additional nucleotides, or (5) have a sequence that differs from that of SEQ ID NO:5 or of SEQ ID NO:6 in having 1, 2, 3, 4, 5, 6, 7, 8, 9, 10 or more than 10 substitution nucleotides in lieu of the nucleotides present in SEQ ID NO:5 or of SEQ ID NO:6, or (6) combinations of such (1)-(5).

Figure 3:
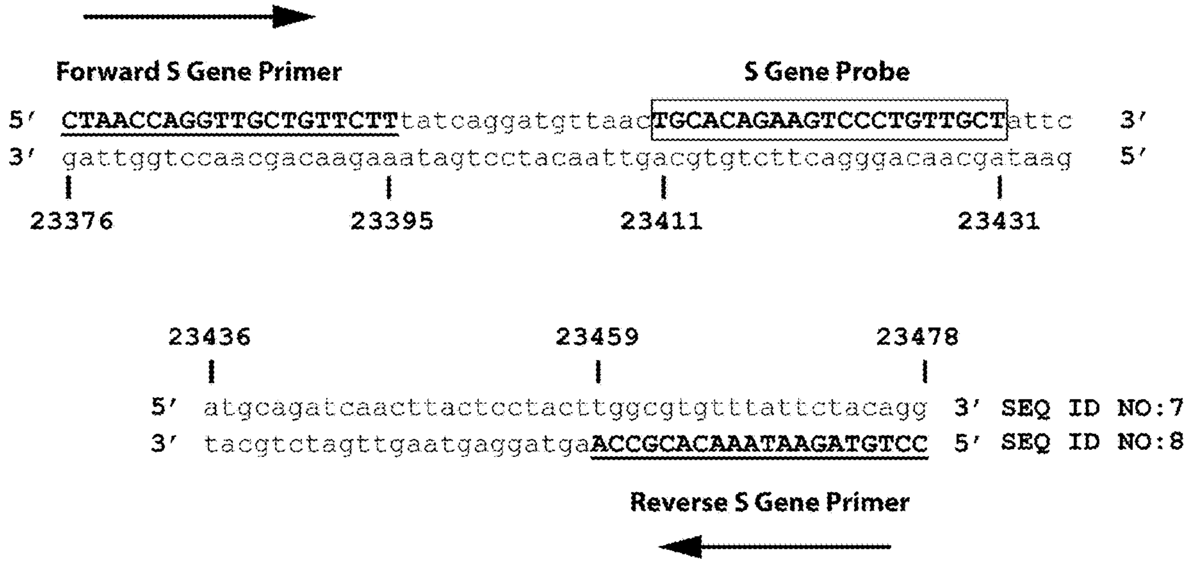
FIG. 3 shows the alignment and orientation of the Forward S Gene Primer and Reverse S Gene Primer of the present invention and the region of the S gene that these primers amplify in an rRT-PCR assay of SARS-CoV-2. Primer sequences are shown in underlined upper case letters; probe sequences are shown in boxed uppercase letters.

The alignment and relative orientation of the Forward S Gene Primer (SEQ ID NO:5) and Reverse S Gene Primer (SEQ ID NO:6) of the present invention and the region of the SARS-CoV-2 S gene that these primers amplify in a rRT-PCR assay of SARS-CoV-2 are shown in FIG. 3.

C. Preferred SARS-CoV-2-Specific Probes

1. Preferred ORF1ab Probe

The preferred probe for detecting the region of ORF1ab that is amplified by the above-described preferred ORF1ab Primers (SEQ ID NO:1 and SEQ ID NO:2) comprises, consists essentially of, or consists of, the nucleotide sequence (SEQ ID NO:9) tgcccgtaatggtgttcttattacaga (the preferred "ORF1ab Probe"). Alternatively, an oligonucleotide that comprises, consists essentially of, or consists of, the complementary nucleotide sequence (SEQ ID NO:10) tctgtaataagaacaccattacgggca could be employed. The alignment and relative position of the preferred ORF1ab Probe of the present invention is shown in FIG. 2.

While it is preferred to detect the presence of the ORF1ab using a probe that consists of the nucleotide sequence of SEQ ID NO:9 or a probe that consists of the nucleotide sequence of SEQ ID NO:10, the invention contemplates that other probes that consist essentially of the nucleotide sequence of SEQ ID NO:9 or SEQ ID NO:10 (in that they possess 1, 2, 3, 4, 5, 6, 7, 8, 9, or 10 additional nucleotide residues, but retain the ability to specifically hybridize to DNA molecules having the nucleotide sequence of SEQ ID NO:3 or SEQ ID NO:4, and more that preferably retain the ability to specifically hybridize to DNA molecules having the nucleotide sequence of SEQ ID NO:9 or SEQ ID NO:10), or "variants" of such probes that retain the ability to specifically hybridize to DNA molecules having the nucleotide sequence of SEQ ID NO:3 or SEQ ID NO:4, and more that preferably retain the ability to specifically hybridize to DNA molecules having the nucleotide sequence of SEQ ID NO:9 or SEQ ID NO:10 could be employed in accordance with the principles and goals of the present invention. Such "Variant ORF1ab Probes" may, for example:

(1) lack 1, 2, 3, 4, 5, 6, 7, 8, 9, or 10 nucleotides of SEQ ID NO:9 or of SEQ ID NO:10, or (2) lack 1, 2, 3, 4, 5, 6, 7, 8, 9, or 10 of the 10 3' terminal nucleotides of the sequence of SEQ ID NO:9 or of SEQ ID NO:10, or (3) lack 1, 2, 3, 4, 5, 6, 7, 8, 9, or 10 of the 10 5' terminal nucleotides of the sequence of SEQ ID NO:9 or of SEQ ID NO:10, or (4) have a sequence that differs from that of SEQ ID NO:9 or of SEQ ID NO:10 in having 1, 2, 3, 4, 5, 6, 7, 8, 9, 10 or more than 10 additional nucleotides, or (5) have a sequence that differs from that of SEQ ID NO:9 or of SEQ ID NO:10 in having 1, 2, 3, 4, 5, 6, 7, 8, 9, 10 or more than 10 substitution nucleotides in lieu of the nucleotides present in SEQ ID NO:9 or of SEQ ID NO:10, or (6) combinations of such (1)-(5).

2. Preferred S Gene Probe

The preferred probe for detecting the region of the S gene that is amplified by the above-described preferred S Gene Primers (SEQ ID NO:5 and SEQ ID NO:6) comprises, consists essentially of, or consists of, the sequence (SEQ ID NO:11) tgcacagaagtccctgttgct (the preferred "S Gene Probe"). Alternatively, an oligonucleotide that comprises, consists essentially of, or consists of, the complementary nucleotide sequence (SEQ ID NO:12) agcaacagggacttctgtgca could be employed. The alignment and relative position of the S Gene Probe of the present invention is shown in FIG. 3.

While it is preferred to detect the presence of the S gene using a probe that consists of the nucleotide sequence of SEQ ID NO:11 or a probe that consists of the nucleotide sequence of SEQ ID NO:12, the invention contemplates that other probes that consist essentially of the nucleotide sequence of SEQ ID NO:11 or SEQ ID NO:12 (in that they possess 1, 2, 3, 4, 5, 6, 7, 8, 9, or 10 additional nucleotide residues, but retain the ability to specifically hybridize to DNA molecules having the nucleotide sequence of SEQ ID NO:7 or SEQ ID NO:8, and more that preferably retain the ability to specifically hybridize to DNA molecules having the nucleotide sequence of SEQ ID NO:11 or SEQ ID NO:12), or "variants" of such probes that retain the ability to specifically hybridize to DNA molecules having the nucleotide sequence of SEQ ID NO:7 or SEQ ID NO:8, and more that preferably retain the ability to specifically hybridize to DNA molecules having the nucleotide sequence of SEQ ID NO:11 or SEQ ID NO:12 could be employed in accordance with the principles and goals of the present invention. Such "Variant S Gene Probes" may, for example:

(1) lack 1, 2, 3, 4, 5, 6, 7, 8, 9, or 10 nucleotides of SEQ ID NO:11 or of SEQ ID NO:12, or
(2) lack 1, 2, 3, 4, 5, 6, 7, 8, 9, or 10 of the 10 3' terminal nucleotides of the sequence of SEQ ID NO:11 or of SEQ ID NO:12, or
(3) lack 1, 2, 3, 4, 5, 6, 7, 8, 9, or 10 of the 10 5' terminal nucleotides of the sequence of SEQ ID NO:11 or of SEQ ID NO:12, or
(4) have a sequence that differs from that of SEQ ID NO:11 or of SEQ ID NO:12 in having 1, 2, 3, 4, 5, 6, 7, 8, 9, 10 or more than 10 additional nucleotides, or
(5) have a sequence that differs from that of SEQ ID NO:11 or of SEQ ID NO:12 in having 1, 2, 3, 4, 5, 6, 7, 8, 9, 10 or more than 10 substitution nucleotides in lieu of the nucleotides present in SEQ ID NO:11 or of SEQ ID NO:12, or
(6) combinations of such (1)-(5).

D. Distinctive Attributes of the Preferred Primers and Probes of the Present Invention The assays of the present invention possess particular distinctive attributes that distinguish such assays from the assays of the prior art. One characteristic of the present invention relates to the use of at least two SARS-CoV-2 target regions as a basis for detection in an rRT-PCR assay. Thus, the rRT-PCR assays of the present invention preferably employ at least two sets of Forward and Reverse primers so as to be capable of specifically and simultaneously amplifying two polynucleotide regions of SARS-CoV-2 RNA. In preferred embodiments, the primers of one of such two sets of primers have sequences that are capable of specifically amplifying a region of ORF1ab, and the primers of the second of such two sets of primers have sequences that are capable of specifically amplifying a region of the S gene.

The use of two amplification targets increases the accuracy of the assays of the present invention since they help ensure that such assays will continue to detect SARS-CoV-2 even if one target becomes eliminated from clinical isolates (for example by spontaneous mutation). The use of two amplification targets also increases the sensitivity of the assay because it is possible that the amplification of a particular target might not provide a detectable concentration of amplified product, for example due to processing or handling issues. By having two targets, the assays of the present invention are more likely to avoid such "false negative" results.

The selection of ORF1ab and the S genes as targets is a further characteristic of the assays of the present invention. These genes are particularly characteristic of SARS-CoV-2, and indeed the targeted region of the SARS-CoV-2 S gene (i.e., its S1 domain) exhibits relatively low homology (only 68%) to the S genes of other coronaviruses (by comparison the ORF1a of SARS-CoV-2 exhibits about 90% homology to the ORF1a of SARS-CoV; the ORF1b of SARS-CoV-2 exhibits about 86% homology to the ORF1b of SARS-CoV (Lu, R. et al. (2020) "*Genomic Characterisation And Epidemiology Of* 2019 *Novel Coronavirus: Implications For Virus Origins And Receptor Binding*," The Lancet 395 (10224):565-574). Thus, it is more likely that the assays of the present invention will not inaccurately amplify sequences of non-SARS-CoV-2 pathogens. Thus, the assays of the present invention are more likely to avoid "false positive" results.

The assays of the present invention employ probes that are unique to SARS-CoV-2 and detect SARS-CoV-2 under conditions in which non-SARS-CoV-2 pathogens are not detected. In a further attribute, the assays of the present invention employ very fast system primers that are designed to mediate the same degree of amplification under the same reaction parameters and temperatures.

The melting temperatures (Tm) of PCR primers determine their kinetics of denaturation from complementary oligonucleotides and their kinetics of annealing to complementary oligonucleotides (see, SantaLucia, J. (1998) *A Unified View Of Polymer, Dumbbell, And Oligonucleotide DNA Nearest-Neighbor Thermodynamics*," Proc. Natl. Acad. Sci. (U.S.A.) 95:1460-1465; von Ahsen, N. et al. (1999) "*Application Of A Thermodynamic Nearest-Neighbor Model To Estimate Nucleic Acid Stability And Optimize Probe Design: Prediction Of Melting Points Of Multiple Mutations Of Apolipoprotein B*-3500 *And Factor V With A Hybridization Probe Genotyping Assay On The Lightcycler*," Clin. Chem. 45(12):2094-2101). Primer pairs that exhibit "substantially identical melting temperatures" (i.e., ±2° C., more preferably, ±1° C., still more preferably ±0.5° C., and most preferably ±0.1° C., as calculated using the method of SantaLucia, J. (1998)) maximize the overall yield of the products that they amplify, and the rate at which such products are produced.

Significantly, the preferred Forward and Reverse ORF1ab Primers of the present invention exhibit such substantially identical melting temperatures, which is a further distinction of the present invention. The preferred Forward ORF1ab Primer has a base-stacking Tm of 58.2° C., whereas the preferred Reverse ORF1ab Primer has a base-stacking Tm of 58.1° C. Thus, the use of the preferred Forward and Reverse ORF1ab Primers of the present invention serves to maximize the overall yield of the amplified ORF1ab product, and the rate at which such product is produced.

The preferred Forward and Reverse S Gene Primers of the present invention also exhibit substantially identical melting temperatures, which is a further distinction of the present invention. The preferred Forward S Gene Primer has a base-stacking Tm of 60° C., whereas the preferred Reverse S Gene Primer has a base-stacking Tm of 59.9° C. Thus, the use of the preferred Forward and Reverse S Gene Primers of the present invention serves to maximize the overall yield of the amplified S Gene product, and the rate at which such product is produced.

Significantly, the melting temperatures of the Forward and Reverse ORF1ab Primers of the present invention are substantially similar to the melting temperature of the preferred Forward and Reverse S Gene Primers of the present invention. Thus, these two sets of preferred primers are extremely well-matched, which is a further distinction of the present invention. Their combined use serves to equalize the overall yield of the amplified ORF1ab and S gene products, which are of similar length (117 nucleotides vs. 103 nucleotides). The substantially similar melting temperatures of the employed sets of primers and the similar lengths of the two amplified products are further distinctions of the present invention.

In designing an rRT-PCR assay, it is desirable for the employed TaqMan probe to have a Tm that is 5-10° C. higher than the employed amplification primers. The employed ORF1ab Probe has a base-stacking Tm of 66.2° C., an 8° C. difference from the Tm of the preferred ORF1ab Primers of the present invention. The employed S Gene Probe has a matching base-stacking Tm of 66.6° C., a 6.6° C. difference from the Tm of the preferred S Gene Primers of the present invention. Thus, each of the preferred TaqMan probes of the present invention exhibit a desired Tm and the two preferred TaqMan probes of the present invention exhibit substantially identical Tms. These are further distinctions of the present invention.

E. Preferred Platform for Conducting the Assays of the Present Invention

In a preferred embodiment, the above-described preferred primers and probes assay the presence of SARS-CoV-2 using a Direct Amplification Disc (DiaSorin Molecular LLC) and SIMPLEXA® Direct Chemistry (DiaSorin Molecular LLC), as processed by a LIAISON® MDX (DiaSorin Molecular LLC) rRt-PCR platform. The operating principles of DiaSorin Molecular LLC's LIAISON® MDX rRt-PCR platform, SIMPLEXA® Direct Chemistry and Direct Amplification Disc are disclosed in U.S. Pat. No. 9,067,205, US Patent Publn. No. 2012/0291565 A1, EP 2499498 B1, EP 2709760 B1, all herein incorporated by reference in their entireties.

In brief, the LIAISON® MDX (DiaSorin) rRt-PCR platform is a compact and portable thermocycler that additionally provides centrifugation and reaction processing capabilities. The device is capable of mediating sample heating (>5° C./sec) and cooling (>4° C./sec), and of regulating temperature to ±0.5° C. (in the range from room temperature to 99° C.). The LIAISON® MDX rRt-PCR platform has the ability to excite fluorescent labels at 475 nm, 475 nm, 520 nm, 580 nm, and 640 nm, and to measure fluorescence at 520 nm, 560 nm, 610 nm and 682 nm, respectively.

The Direct Amplification Disc is radially oriented, multi-chambered, fluidic device that is capable of processing the amplification of target sequences (if present) in up to 8 (50 μL) clinical samples at a time. The samples may be provided directly to the Direct Amplification Disc, as cellular material or lysates, without any prior DNA or RNA extraction.

In brief, an aliquot of the clinical sample and reaction reagents (i.e., a DNA polymerase, a reverse transcriptase, one or more pairs of SARS-CoV-2-specific primers (preferably, the above-discussed preferred Forward and Reverse ORF1ab Primers and the above-discussed preferred Forward and Reverse S Gene Primers, two or more SARS-CoV-2-specific probes (preferably, the above-discussed preferred ORF1ab Probe and the above-discussed preferred S Gene Probe), and deoxynucleotide triphosphates (dNTPs) and buffers) are separately provided to a provision area of the Direct Amplification Disc (see, U.S. Pat. No. 9,067,205, US Patent Publn No. 2012/0291565 A1, EP 2709760 B1). Preferably, the reaction reagents required for rRT-PCR are provided using "master mixes," which are widely available commercially (Applied Biosystems; ThermoFisher Scientific, etc.). Primers may be provided at a concentration of between 0.1 and 0.5 μM (5-25 pmol/per 50 μl reaction). Probe molecules may be provided at a concentration of between 0.05 and 0.25 μM (2.5-12.5 pmol/per 50 μl reaction).

The LIAISON® MDX device centrifuges the Direct Amplification Disc to thereby force a portion of the sample and reagents to be separately moved into reservoirs for a reaction chamber. The centrifugation moves any excess sample or reagents to a holding chamber. A laser within the LIAISON® MDX device then opens a first valve permitting the sample to flow into the reaction chamber. The chamber is then heated (for example to 95° C.); the high temperature and centrifugation serves to lyse cells that may be present in the sample. The laser within the LIAISON® MDX device then opens a second valve permitting reagents sample to flow into the reaction chamber and mix with the sample. The LIAISON® MDX device then commences to subject the reaction to PCR thermocycling. An internal control may be used to monitor successful instrument and sample processing and to detect RT-PCR failure and/or inhibition.

An internal control may be employed in order to confirm that the reaction conditions are suitable for target amplification and detection. A suitable internal control, for example, is one that amplifies MS2 phage sequences. A suitable Forward MS2 Phage Internal Control Primer has the sequence (SEQ ID NO:13 tgctcgcggatacccg); a suitable Reverse MS2 Phage Internal Control Primer has the sequence (SEQ ID NO:14 aacttgcgttctcgagcgat). Amplification mediated by such internal control primers may be detected using a TaqMan probe (MS2 Phage Internal Control Probe) having the sequence (SEQ ID NO:15 acctcgggtttc-cgtcttgctcgt. Alternatively, other MS2 internal control primers may be employed (Dreier, J. et al. (2005) "Use of Bacteriophage MS2 as an Internal Control in Viral Reverse Transcription-PCR Assays," J. Clin. Microbiol. 43(9):4551-4557). The probe may be labeled with the Quasar 670 fluorophore and complexed with the BHQ2 quencher, or with any other fluorophore and any quencher capable of quenching the fluorescence of such fluorophore.

The LIAISON MDX Software runs a pre-heating cycle to denature the SARS-CoV-2 viral coat protein and thereby release the SARS-CoV-2 RNA. This step is followed by reverse transcription and subsequent amplification. During the extension phase of the PCR cycle, the 5' nuclease activity of DNA polymerase degrades any probe that has hybridized to amplified product in the reaction, thereby causing the fluorescent label of the probe to separate from the quencher of the probe. Such separation permits a fluorescent signal to be detected. With each cycle, additional fluorescent label molecules are cleaved from their respective probes, increasing the fluorescence intensity.

Reaction results are monitored and presented to users via LIAISON® MDX's software. Such software provides easy to understand results with the ability to check amplification curves after a run. The software also plots QC Charts and can be bi-directionally interfaced with LIS for easy integration into 1ab workflow. The LIAISON® MDX permit random access to individual samples, and thus allows users to start the analysis of new samples without waiting for previously-started analyses to complete. Assay results can be obtained in one hour or less. Table 1 shows the Diagnostic Algorithm of the assay.

TABLE 1

| SARS-CoV-2 $C_T$ value (ORF1ab Target) | SARS-CoV-2 $C_T$ value (S Gene Target) | RNA IC $C_T$ value | Interpretation |
|---|---|---|---|
| ≤40, ≠0 | ≤40, ≠0 | N/A | SARS-CoV-2 RNA: Detected |

TABLE 1-continued

| SARS-CoV-2 $C_T$ value (ORF1ab Target) | SARS-CoV-2 $C_T$ value (S Gene Target) | RNA IC $C_T$ value | Interpretation |
|---|---|---|---|
| ≤40, ≠0 | N/A | N/A | SARS-CoV-2 RNA: Detected |
| N/A | ≤40, ≠0 | N/A | SARS-CoV-2 RNA: Detected |
| 0 | 0 | ≤40, ≠0 | SARS-CoV-2 RNA: Not Detected |
| 0 | 0 | 0 | Results Invalid Repeat Assay: If RNA IC is still 0 on repeat, test with a new sample if clinically warranted |

Accordingly, if the ORF1ab and the S gene CT values are both ≤40 for a patient specimen, the result is reported as "Detected" for the SARS-CoV-2 RNA. The internal control is not applicable. If the ORF1ab CT value is ≤40 and the S gene CT value is 0 for a patient specimen, the result is reported as "Detected" for the SARS-CoV-2 RNA. The internal control is not applicable. If the ORF1ab CT value is 0 and the S gene CT value is ≤40 for a patient specimen, the result is reported as "Detected" for the SARS-CoV-2 RNA. The internal control is not applicable. If the ORF1ab and the S gene CT values are both 0 for a patient specimen and the internal control CT is non-zero and ≤45, the result is reported as "Not Detected" for the SARS-CoV-2 RNA. If the ORF1ab and the S gene CT values are both 0 for a patient specimen and the internal control CT is also 0, the result is reported as "Invalid." This specimen should be re-assayed. If the internal control is still 0 for the repeated assay, the test should be repeated with a new sample, if clinically warranted.

F. Kits

The invention additionally includes kits for conducting the above-described assays. In one embodiment, such kits will include one or more containers containing reagents for specifically detecting the SARS-CoV-2 ORF1ab (e.g., a Forward ORF1ab Primer, a Reverse ORF1ab Primer, and an ORF1ab Probe) and instructions for the use of such reagents to detect SARS-CoV-2. Such kits may comprise a Variant Forward ORF1ab Primer, a Variant Reverse ORF1ab Primer, and/or a Variant ORF1ab Probe. Most preferably, such kits will comprise the above-described preferred ORF1ab Forward Primer, the above-described preferred ORF1ab Reverse Primer and the above-described preferred ORF1ab Probe.

In a second embodiment, such kits will include one or more containers containing reagents for specifically detecting the SARS-CoV-2 S gene (e.g., a Forward S Gene Primer, a Reverse S Gene Primer, and an S Gene Probe) and instructions for the use of such reagents to detect SARS-CoV-2. Such kits may comprise a Variant Forward S Gene Primer, a Variant Reverse S Gene Primer, and/or a Variant S Gene Probe. Most preferably, such kits will comprise the above-described preferred S Gene Forward Primer, the above-described preferred S Gene Reverse Primer and the above-described preferred S Gene Probe.

In a third embodiment, such kits will include one or more containers containing reagents for specifically detecting both the SARS-CoV-2 ORF1ab and the SARS-CoV-2 S gene (e.g., a Forward ORF1ab Primer, a Reverse ORF1ab Primer, an ORF1ab Probe, a Forward S Gene Primer, a Reverse S Gene Primer, and an S Gene Probe) and instructions for the use of such reagents to detect SARS-CoV-2, and will most preferably comprise the above-described preferred ORF1ab Forward Primer, the above-described preferred ORF1ab Reverse Primer, the above-described preferred ORF1ab Probe, the above-described preferred S Gene Forward Primer, the above-described preferred S Gene Reverse Primer and the above-described preferred S Gene Probe.

The containers of such kits will be vials, tubes, etc. and the reagents may be in liquid form or may be lyophilized. Alternatively, such containers will be a multi-chambered, fluidic device that is capable of processing the amplification of such primers. For example, the kits of the present invention may be a Direct Amplification Disc (U.S. Pat. No. 9,067,205) that has been preloaded with reagents for amplifying the above-described SARS-CoV-2 gene sequences.

G. Embodiments of the Invention

Having now generally described the invention, the same will be more readily understood through reference to the following numbered Embodiments ("E"), which are provided by way of illustration and are not intended to be limiting of the present invention unless specified:

E1. An oligonucleotide, having a 5' terminus and a 3' terminus, wherein the oligonucleotide has a nucleotide sequence that consists of, consists essentially of, or is a variant of, the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:12.

E2. An oligonucleotide, having a 5' terminus and a 3' terminus, wherein the oligonucleotide has a nucleotide sequence that consists of the nucleotide sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 or SEQ ID NO:12.

E3. The oligonucleotide of E1 or E2, wherein the oligonucleotide has a nucleotide sequence that consists of, or consists essentially of, or is a variant of, the nucleotide sequence of SEQ ID NO: 1.

E4. The oligonucleotide of E1 or E2, wherein the oligonucleotide has a nucleotide sequence that consists of, or consists essentially of, or is a variant of, the nucleotide sequence of SEQ ID NO:2.

E5. The oligonucleotide of E1 or E2, wherein the oligonucleotide has a nucleotide sequence that consists of, or consists essentially of, or is a variant of, the nucleotide sequence of SEQ ID NO:3.

E6. The oligonucleotide of E1 or E2, wherein the oligonucleotide has a nucleotide sequence that consists of, or consists essentially of, or is a variant of, the nucleotide sequence of SEQ ID NO:4.

E7. The oligonucleotide of E1 or E2, wherein the oligonucleotide has a nucleotide sequence that consists of, or consists essentially of, or is a variant of, the nucleotide sequence of SEQ ID NO:5.

E8. The oligonucleotide of E1 or E2, wherein the oligonucleotide has a nucleotide sequence that consists of, or consists essentially of, or is a variant of, the nucleotide sequence of SEQ ID NO:6.

E9. The oligonucleotide of E1 or E2, wherein the oligonucleotide has a nucleotide sequence that consists of, or consists essentially of, or is a variant of, the nucleotide sequence of SEQ ID NO:7.

E10. The oligonucleotide of E1 or E2, wherein the oligonucleotide has a nucleotide sequence that consists of, or consists essentially of, or is a variant of, the nucleotide sequence of SEQ ID NO:8.

E11. The oligonucleotide of E1 or E2, wherein the oligonucleotide has a nucleotide sequence that consists of, or consists essentially of, or is a variant of, the nucleotide sequence of SEQ ID NO:9.

E12. The oligonucleotide of E1 or E2, wherein the oligonucleotide has a nucleotide sequence that consists of, or consists essentially of, or is a variant of, the nucleotide sequence of SEQ ID NO:10.

E13. The oligonucleotide of E1 or E2, wherein the oligonucleotide has a nucleotide sequence that consists of, or consists essentially of, or is a variant of, the nucleotide sequence of SEQ ID NO:11.

E14. The oligonucleotide of E1 or E2, wherein the oligonucleotide has a nucleotide sequence that consists of, or consists essentially of, or is a variant of, the nucleotide sequence of SEQ ID NO:12.

E15. The oligonucleotide of E1, wherein the oligonucleotide has a nucleotide sequence that consists of, or consists essentially of, or is a variant of, the nucleotide sequence of SEQ ID NO:9 or the nucleotide sequence of SEQ ID NO:10, wherein the oligonucleotide has a 5' terminus that is labeled with a fluorophore and a 3' terminus that is complexed to a quencher of fluorescence of the fluorophore.

E16. The oligonucleotide of E15, wherein the fluorophore has an excitation wavelength within the range of about 352-690 nm and an emission wavelength within the range of about 447-705 nm.

E17. The oligonucleotide of E15, wherein the fluorophore is FAM or JOE.

E18. The oligonucleotide of E1, wherein the oligonucleotide has a nucleotide sequence that consists of, consists essentially of, or is a variant of, the nucleotide sequence of SEQ ID NO:11 or the nucleotide sequence of SEQ ID NO:12, wherein the oligonucleotide has a 5' terminus that is labeled with a fluorophore and a 3' terminus that is complexed to a quencher of fluorescence of the fluorophore.

E19. The oligonucleotide of E18, wherein the fluorophore has an excitation wavelength within the range of about 352-690 nm and an emission wavelength within the range of about 447-705 nm.

E20. The oligonucleotide of E18, wherein the fluorophore is FAM or JOE.

E21. A method for detecting the presence of SARS-CoV-2 in a clinical sample, wherein the method comprises:

(I) incubating the clinical sample in vitro in the presence of:

(1) a reverse transcriptase and a DNA polymerase having a 5'→3' exonuclease activity; and (2) a Forward ORF1ab Primer having a nucleotide sequence that consists of, consists essentially of, or is a variant of, the nucleotide sequence of SEQ ID NO:1;

(3) a Reverse ORF1ab Primer having a nucleotide sequence that consists of, consists essentially of, or is a variant of, the nucleotide sequence of SEQ ID NO:2; and (4) an ORF1ab Probe, the ORF1ab Probe being an oligonucleotide having a nucleotide sequence that consists of, consists essentially of, or is a variant of, the nucleotide sequence of SEQ ID NO:9 or SEQ ID NO:10, wherein the ORF1ab Probe oligonucleotide has a 5' terminus that is labeled with a fluorophore and a 3' terminus that is complexed to a quencher of fluorescence of the fluorophore; and wherein the incubation is in a reaction under conditions sufficient to permit:

(a) the Forward and Reverse ORF1ab Primers to mediate a polymerase chain reaction amplification of a region of the ORF1ab of SARS-CoV-2 to thereby produce amplified ORF1ab oligonucleotide molecules, if the SARS-CoV-2 is present in the clinical sample;

(b) the ORF1ab Probe to hybridize to amplified ORF1ab oligonucleotide molecules; and (c) the 5'→3' exonuclease activity to hydrolyze hybridized ORF1ab Probe, to thereby separate the fluorophore thereof from the quencher thereof and cause a fluorescent signal to become detectable; and (II) determining whether the SARS-CoV-2 is present in the clinical sample by determining whether a fluorescent signal of the fluorophore has become detectable.

E22. The method of E21, wherein the fluorophore has an excitation wavelength within the range of about 352-690 nm and an emission wavelength within the range of about 447-705 nm.

E23. The method of E21, wherein the fluorophore is FAM or JOE.

E24. A method for detecting the presence of SARS-CoV-2 in a clinical sample, wherein the method comprises:

(I) incubating the clinical sample in vitro in the presence of:

(1) a reverse transcriptase and a DNA polymerase having a 5'→3' exonuclease activity; and (2) a Forward S Gene Primer having a nucleotide sequence that consists of, consists essentially of, or is a variant of, the nucleotide sequence of SEQ ID NO:5;

(3) a Reverse S Gene Primer having a nucleotide sequence that consists of, consists essentially of, or is a variant of, the nucleotide sequence of SEQ ID NO:6; and (4) an S Gene Probe, the S Gene Probe being an oligonucleotide having a nucleotide sequence that consists of, consists essentially of, or is a variant of, the nucleotide sequence of SEQ ID NO:11 or SEQ ID NO:12, wherein the S Gene Probe oligonucleotide has a 5' terminus that is labeled with a fluorophore and a 3' terminus that is complexed to a quencher of fluorescence of the fluorophore; and wherein the incubation is in a reaction under conditions sufficient to permit:

(a) the Forward and Reverse S Gene Primers to mediate a polymerase chain reaction amplification of a region of the S gene of SARS-CoV-2 to thereby produce amplified S gene oligonucleotide molecules, if the SARS-CoV-2 is present in the clinical sample;

(b) the S Gene Probe to hybridize to amplified S gene oligonucleotide molecules; and (c) the 5'→3' exonuclease activity to hydrolyze hybridized S Gene Probe, to thereby separate the fluorophore thereof from the quencher thereof and cause a fluorescent signal to become detectable; and (II) determining whether the SARS-CoV-2 is present in the clinical sample by determining whether a fluorescent signal of the fluorophore has become detectable.

E25. The method of E24, wherein the fluorophore has an excitation wavelength within the range of about 352-690 nm and an emission wavelength within the range of about 447-705 nm.

E26. The method of E24, wherein the fluorophore is FAM or JOE.

E27. A method for detecting the presence of SARS-CoV-2 in a clinical sample, wherein the method comprises:

(I) incubating the clinical sample in vitro in the presence of:

(1) a reverse transcriptase and a DNA polymerase having a 5'→3' exonuclease activity; and (2) a Forward S Gene Primer having a nucleotide sequence that consists of, consists essentially of, or is a variant of, the nucleotide sequence of SEQ ID NO:5;

(3) a Reverse S Gene Primer having a nucleotide sequence that consists of, consists essentially of, or is a variant of, the nucleotide sequence of SEQ ID NO:6;

(4) an S Gene Probe, the S Gene Probe being an oligonucleotide having a nucleotide sequence that consists of, consists essentially of, or is a variant of, the nucleotide sequence of SEQ ID NO:11 or SEQ ID NO:12, wherein the S Gene Probe oligonucleotide has a 5' terminus that is labeled with a fluorophore and a 3' terminus that is complexed to a quencher of fluorescence of the fluorophore;

(5) a Forward ORF1ab Primer having a nucleotide sequence that consists of, consists essentially of, or is a variant of, the nucleotide sequence of SEQ ID NO:1;

(6) a Reverse ORF1ab Primer having a nucleotide sequence that consists of, consists essentially of, or is a variant of, the nucleotide sequence of SEQ ID NO:2; and (7) an ORF1ab Probe, the ORF1ab Probe being an oligonucleotide having a nucleotide sequence that consists of, consists essentially of, or is a variant of, the nucleotide sequence of SEQ ID NO:9 or SEQ ID NO:10, wherein the ORF1ab Probe oligonucleotide has a 5' terminus that is labeled with a fluorophore and a 3' terminus that is complexed to a quencher of fluorescence of the fluorophore; wherein the fluorescence of the fluorophore of the ORF1ab Probe is distinguishable from the fluorescence of the fluorophore of the S Gene Probe; and wherein the incubation is in a reaction under conditions sufficient to permit:

(a) the Forward and Reverse S Gene Primers to mediate a polymerase chain reaction amplification of a region of the S gene of SARS-CoV-2 to thereby produce amplified S gene oligonucleotide molecules, if the SARS-CoV-2 is present in the clinical sample;

(b) the S Gene Probe to hybridize to amplified S gene oligonucleotide molecules; and (c) the 5'→3' exonuclease activity to hydrolyze hybridized S Gene Probe, to thereby separate the fluorophore thereof from the quencher thereof and cause a fluorescent signal to become detectable; and (II) determining whether the SARS-CoV-2 is present in the clinical sample by determining whether a fluorescent signal of the fluorophore has become detectable.

E28. The method of E24, wherein the clinical sample is incubated in the additional presence of:

(5) a Forward ORF1ab Primer having a nucleotide sequence that consists of, consists essentially of, or is a variant of, the nucleotide sequence of SEQ ID NO:1;

(6) a Reverse ORF1ab Primer having a nucleotide sequence that consists of, consists essentially of, or is a variant of, the nucleotide sequence of SEQ ID NO:2; and (7) an ORF1 ab Probe, the ORF1ab Probe being an oligonucleotide having a nucleotide sequence that consists of, consists essentially of, or is a variant of the nucleotide sequence of SEQ ID NO:9 or SEQ ID NO:10, wherein the ORF1ab Probe oligonucleotide has a 5' terminus that is labeled with a fluorophore and a 3' terminus that is complexed to a quencher of fluorescence of the fluorophore; wherein the fluorescence of the fluorophore of the ORF1ab Probe is distinguishable from the fluorescence of the fluorophore of the S Gene Probe; and wherein the reaction is additionally incubated under conditions sufficient to permit:

(a) the Forward and Reverse ORF1ab Primers to mediate a polymerase chain reaction amplification of a region of the ORF1ab of SARS-CoV-2 to thereby produce amplified ORF1ab oligonucleotide molecules, if the SARS-CoV-2 is present in the clinical sample;

(b) the ORF1ab Probe to hybridize to amplified ORF1 ab oligonucleotide molecules; and (c) the 5'→3' exonuclease activity to hydrolyze hybridized ORF1ab Probe, to thereby separate the fluorophore thereof from the quencher thereof and cause a fluorescent signal to become detectable; and wherein said SARS-CoV-2 is determined to be present in said clinical sample by determining whether a fluorescent signal of at least one of said ORF1ab Probe or said S Gene Probe fluorophores has become detectable.

E29. The method of E28, wherein the fluorophore of the ORF1ab Probe and the fluorophore of the S Gene Probe have an excitation wavelength within the range of about 352-690 nm and an emission wavelength within the range of about 447-705 nm.

E30. The method of E28, wherein one of the fluorophores of the ORF1ab Probe and the S Gene Probe is JOE and the other of such fluorophores is FAM.

E31. A kit for detecting the presence of SARS-CoV-2 in a clinical sample, wherein the kit comprises:

(I) reagents for detecting SARS-CoV-2 ORF1ab, wherein the SARS-CoV-2 ORF1ab detection reagents comprise:

(1) a Forward ORF1ab Primer having a nucleotide sequence that consists of, consists essentially of, or is a variant of, the nucleotide sequence of SEQ ID NO:1;

(2) a Reverse ORF1ab Primer having a nucleotide sequence that consists of, consists essentially of, or is a variant of, the nucleotide sequence of SEQ ID NO:2; and (3) an ORF1ab Probe, the ORF1ab Probe being an oligonucleotide having a nucleotide sequence that consists of, consists essentially of, or is a variant of, the nucleotide sequence of SEQ ID NO:9 or SEQ ID NO:10, wherein the ORF1ab Probe oligonucleotide has a 5' terminus that is labeled with a fluorophore and a 3' terminus that is complexed to a quencher of fluorescence of the fluorophore; and (II) instructions for using such detection reagents to detect the presence of SARS-CoV-2 in the clinical sample.

E32. The kit of E31, wherein the fluorophore of the ORF1ab Probe has an excitation wavelength within the range of about 352-690 nm and an emission wavelength within the range of about 447-705 nm.

E33. The kit of E31, wherein the fluorophore of the ORF1ab is JOE or FAM.

E34. A kit for detecting the presence of SARS-CoV-2 in a clinical sample, wherein the kit comprises:

(I) reagents for detecting SARS-CoV-2 S gene, wherein the SARS-CoV-2 S gene detection reagents comprise:

(1) a Forward S Gene Primer having a nucleotide sequence that consists of, consists essentially of, or is a variant of, the nucleotide sequence of SEQ ID NO:5;

(2) a Reverse S Gene Primer having a nucleotide sequence that consists of, consists essentially of, or is a variant of, the nucleotide sequence of SEQ ID NO:6; and (3) an S Gene Probe, the S Gene Probe being an oligonucleotide having a nucleotide sequence that consists of, consists essentially of, or is a variant of, the nucleotide sequence of SEQ ID NO:11 or SEQ ID NO:12, wherein the S Gene Probe oligonucleotide has a 5' terminus that is labeled with a fluorophore and a 3' terminus that is complexed to a quencher of fluorescence of the fluorophore; and (II) instructions for using such detection reagents to detect the presence of SARS-CoV-2 in the clinical sample.

E35. The kit of E34, wherein the fluorophore of the S Gene Probe has an excitation wavelength within the range of about 352-690 nm and an emission wavelength within the range of about 447-705 nm.

E36. The kit of E34, wherein the fluorophore of the S Gene is JOE or FAM.

E37. A kit for detecting the presence of SARS-CoV-2 in a clinical sample, wherein the kit comprises:

(I) (A) reagents for detecting SARS-CoV-2 ORF1ab, wherein the SARS-CoV-2 ORF1ab detection reagents comprise:

(1) a Forward ORF1ab Primer having a nucleotide sequence that consists of, consists essentially of, or is a variant of, the nucleotide sequence of SEQ ID NO:1;

(2) a Reverse ORF1ab Primer having a nucleotide sequence that consists of, consists essentially of, or is a variant of, the nucleotide sequence of SEQ ID NO:2; and (3) an ORF1ab Probe, the ORF1ab Probe being an oligonucleotide having a nucleotide sequence that consists of, consists essentially of, or is a variant of, the nucleotide sequence of SEQ ID NO:9 or SEQ ID NO:10, wherein the ORF1ab Probe oligonucleotide has a 5' terminus that is labeled with a fluorophore and a 3' terminus that is complexed to a quencher of fluorescence of the fluorophore; and (B) reagents for detecting SARS-CoV-2 S gene, wherein the SARS-CoV-2 S gene detection reagents comprise:

(1) a Forward S Gene Primer having a nucleotide sequence that consists of, consists essentially of, or is a variant of, the nucleotide sequence of SEQ ID NO:5;

(2) a Reverse S Gene Primer having a nucleotide sequence that consists of, consists essentially of, or is a variant of, the nucleotide sequence of SEQ ID NO:6; and (3) an S Gene Probe, the S Gene Probe being an oligonucleotide having a nucleotide sequence that consists of, consists essentially of, or is a variant of, the nucleotide sequence of SEQ ID NO:11 or SEQ ID NO:12, wherein the S Gene Probe oligonucleotide has a 5' terminus that is labeled with a fluorophore and a 3' terminus that is complexed to a quencher of fluorescence of the fluorophore; wherein the fluorescence of the fluorophore of the S Gene Probe is distinguishable from the fluorescence of the fluorophore of the ORF1ab Probe; and (II) instructions for using such reagent to detect the presence of SARS-CoV-2 in the clinical sample.

E38. The kit of E37, wherein the fluorophore of the ORF1ab Probe and the fluorophore of the S Gene Probe each have an excitation wavelength within the range of about 352-690 nm and an emission wavelength within the range of about 447-705 nm.

E39. The kit of E37, wherein one of the fluorophores of the ORF1ab Probe and the S Gene Probe is JOE and the other of such fluorophores is FAM.

EXAMPLES

Having now generally described the invention, the same will be more readily understood through reference to the following examples, which are provided by way of illustration and are not intended to be limiting of the present invention unless specified.

Example 1

Design of the Preferred Primers and Probes

Two sets of primers and probes were designed for the specific detection of SARS-CoV-2. Each primer/probe set on its own has been shown to provide sensitive and specific detection of SARS-CoV-2 with no detection or cross-reactivity to other coronaviruses. The SARS-CoV-2 Reference Sequence (NC_045512.2; Wuhan seafood market pneumonia virus isolate Wuhan-Hu-1, complete genome) was used to design such primers and probes.

The genome alignment of CoVs shows 58% identity of non-structural protein-coding region and 43% identity of structural proteins-coding region among different coronaviruses, with 54% identity at the whole genome level. This suggests that the non-structural proteins are more conserved and that the structural proteins exhibit greater diversity to fit their different environments (Chen, Y, et al. (2020) "*Emerging Coronaviruses: Genome Structure, Replication, And Pathogenesis*," J. Med. Virol. 92:418-423).

An analysis was conducted comparing the sequence of SARS-CoV-2 to the sequences of six other CoVs that can infect humans and cause respiratory diseases, in order to select a region that would be able to detect and specifically discriminate SARS-CoV-2 from such other CoVs. The analysis focused on genomic regions coding for structural proteins that are unique to this virus (Ji, W. et al. (2020) "*Cross*-Species *Transmission Of The Newly Identified Coronavirus* 2019-*nCoV*," J Med. Virol. 92:433-440). However, since it is possible that such regions might frequently recombine, in parallel, primers were designed against genomic regions coding for non-structural proteins.

Regarding the selection of the S gene, the SARS-CoV-2 may be generated by a homologous recombination within a region spanning between position 21500 and 24000 (2500 bp), which covers most of the S gene sequence (Chen, Y, et al. (2020) "*Emerging Coronaviruses: Genome Structure, Replication, And Pathogenesis*," J. Med. Virol. 92:418-423). In particular, inside the 2500 bp region, Chen, Y, et al. (2020) identified a unique sequence corresponding to the first 783 nucleotides at the 5' end of the S gene. BLAST analysis of a 783 nucleotide fragment provided no match with any sequence present in NCBI database, apart from the Wuhan seafood market pneumonia virus isolate Wuhan-Hu-14.

Regarding the selection of the ORF1ab sequence, the SARS-CoV-2 has a characteristic non-structural protein-coding region, covering about two-thirds of its genome length, and encoding 16 non-structural proteins (nsp1-16); the sequence shows 58% identity to the sequences of other CoVs (Chen, Y, et al. (2020) "*Emerging Coronaviruses: Genome Structure, Replication, And Pathogenesis*," J. Med. Virol. 92:418-423). This approximately 20 kb region was chosen for the design of different primer sets specific for SARS-CoV-2.

All primer sets designed to target ORF1ab and the S gene have been tested on the SARS-CoV2 complete genome sequences available in the Global Initiative on Sharing All Influenza Data (GISAID) database, using Geneious Prime software. Sequences were mapped to the Reference Sequence of SARS-CoV-2 (NC_045512.2), and the identified primers and probes were tested against the consensus. The analysis showed that all regions recognized by the identified primers and probes have a homology of 100% with all available SARS-CoV-2 sequences.

In addition to verifying the specificity of the design, the sequences of the six CoVs that can infect humans causing respiratory diseases (i.e., HCoV-229E, HCoV-OC43, HCoV-NL63, HKU1, SARS-CoV and MERS-CoV) were examined. The accession numbers for such sequences are: NC_002645.1 (Human coronavirus 229E); NC 006213.1 (Human coronavirus OC43 strain ATCC VR-759); NC_005831.2 (Human Coronavirus NL63), NC_006577.2 (Human coronavirus HKU1), NC_004718.3 (SARS-coronavirus), and NC_019843.3 (Middle East Respiratory Syndrome coronavirus).

The sequences of the above-described preferred Forward and Reverse ORF1 ab Primers (SEQ ID NO:1 and SEQ ID NO:2, respectively), the above-described preferred Forward and Reverse S Gene Primers (SEQ ID NO:5 and SEQ ID NO:6, respectively), the above-described preferred ORF1ab Probe (SEQ ID NO:9) and the above-described preferred S Gene Probe (SEQ ID NO:11) were identified through such an analysis.

Example 2

Specificity of the SARS-CoV-2 Assay

Upon in silico analysis, a SIMPLEXA™ SARS-CoV-2 Direct assay using the above-described preferred Forward and Reverse ORF1ab and S Gene Primers and the above-described preferred ORF1ab and S Gene Probes were found to detect all SARS-CoV-2 virus strains and to exhibit no cross-reactivity with non-SARS-CoV-2 species.

In addition to the in silico analysis, an in vitro analysis of specificity was performed. The results of the in vitro specimen testing are presented in Table 2.

TABLE 2

| | | Qualitative % Detection (# Detected/# Tested) | | |
|---|---|---|---|---|
| Organism | Tested Concentration | S Gene (FAM) | ORF1ab (JOE) | Internal Control (Q670) |
| Adenovirus 1 | 1 × $10^5$ U/mL | 0% (0/3) | 0% (0/3) | 100% (3/3) |
| *Bordetella pertussis* | 1 × $10^6$ CFU/mL | 0% (0/3) | 0% (0/3) | 100% (3/3) |
| *Chlamydophila pneumoniae* | 1 × $10^6$ IFU/mL | 0% (0/3) | 0% (0/3) | 100% (3/3) |
| Coronavirus 229E | 1 × $10^5$ $TCID_{50}$/mL | 0% (0/3) | 0% (0/3) | 100% (3/3) |
| Coronavirus NL63 | 1 × $10^5$ U/mL | 0% (0/3) | 0% (0/3) | 100% (3/3) |
| Coronavirus OC43 | 1 × $10^5$ $TCID_{50}$/mL | 0% (0/3) | 0% (0/3) | 100% (3/3) |
| Enterovirus 68 | 1 × $10^5$ $TCID_{50}$/mL | 0% (0/3) | 0% (0/3) | 100% (3/3) |
| *Haemophilus influenzae* | 1 × $10^6$ CFU/mL | 0% (0/3) | 0% (0/3) | 100% (3/3) |
| Human metapneumovirus (hMPV-9) | 1 × $10^5$ $TCID_{50}$/mL | 0% (0/3) | 0% (0/3) | 100% (3/3) |
| Influenza A H3N2 Hong Kong 8/68 | 1 × $10^5$ $TCID_{50}$/mL | 0% (0/3) | 0% (0/3) | 100% (3/3) |
| Influenza B Phuket 3073/2013 | 1 × $10^5$ $TCID_{50}$/mL | 0% (0/3) | 0% (0/3) | 100% (3/3) |
| *Legionella pneumophilia* | 1 × $10^6$ CFU/mL | 0% (0/3) | 0% (0/3) | 100% (3/3) |
| MERS-Coronavirus (Extracted RNA) | 1:3 dilution | 0% (0/3) | 0% (0/3) | 100% (3/3) |
| *Mycobacterium tuberculosis* (Genomic DNA) | 1 × $10^6$ copies/mL | 0% (0/3) | 0% (0/3) | 100% (3/3) |
| Parainfluenza Type 1 | 1 × $10^5$ U/mL | 0% (0/3) | 0% (0/3) | 100% (3/3) |
| Parainfluenza Type 2 | 1 × $10^5$ U/mL | 0% (0/3) | 0% (0/3) | 100% (3/3) |
| Parainfluenza Type 3 | 1 × $10^5$ $TCID_{50}$/mL | 0% (0/3) | 0% (0/3) | 100% (3/3) |
| Parainfluenza Type 4A | 1 × $10^5$ U/mL | 0% (0/3) | 0% (0/3) | 100% (3/3) |
| Rhinovirus B14 | 1 × $10^5$ U/mL | 0% (0/3) | 0% (0/3) | 100% (3/3) |
| RSV A Long | 1 × $10^5$ $TCID_{50}$/mL | 0% (0/3) | 0% (0/3) | 100% (3/3) |
| RSV B Washington | 1 × $10^5$ $TCID_{50}$/mL | 0% (0/3) | 0% (0/3) | 100% (3/3) |
| SARS-Coronavirus (Purified RNA) | 1 × $10^5$ copies/mL | 0% (0/3) | 0% (0/3) | 100% (3/3) |
| SARS-Coronavirus HKU39849 (Extracted RNA) | 1:10 dilution | 0% (0/3) | 0% (0/3) | 100% (3/3) |
| *Streptococcus pneumoniae* | 1 × $10^6$ CFU/mL | 0% (0/3) | 0% (0/3) | 100% (3/3) |
| *Streptococcus pyogenes* | 1 × $10^6$ CFU/mL | 0% (0/3) | 0% (0/3) | 100% (3/3) |
| Human leukocytes (human genomic DNA) | 1 × $10^6$ cells/mL | 0% (0/3) | 0% (0/3) | 100% (3/3) |
| Pooled Human Nasal Fluid | 1:5 dilution | 0% (0/3) | 0% (0/3) | 100% (3/3) |

The assay was also found to demonstrate 100% specificity on a negative matrix (Universal Transport Medium (UTM); Copan Diagnostics). No not-specific signals were observed.

In conclusion, the above-described preferred Forward and Reverse ORF1ab Primers and the above-described preferred ORF1ab Probe were found to be capable of detecting SARS-CoV-2 without exhibiting cross-reactivity to human DNA, or to DNA (or cDNA) of other pathogens. Additionally, the above-described preferred Forward and Reverse S Gene Primers and the above-described preferred S Gene Probe were found to be capable of detecting SARS-CoV-2 without exhibiting cross-reactivity to human DNA, or to DNA (or cDNA) of other pathogens. The assay is thus specific for SARS-CoV-2.

The observation that the assay of the present invention reports the detection of SARS-CoV-2 when only one of such sets of primers and probes is employed (i.e., either a probe and primer set that targets ORF1ab or a probe and primer set that targets the S gene) indicates that by using both such sets of probes and primers, one can increase assay sensitivity in cases of low viral loads and that the accuracy of the assay will not be jeopardized by any point mutation which may occur during COVID-19 spread across the population.

To demonstrate the improvement in assay sensitivity obtained using both sets of preferred primers and probes, a preparation of SARS-CoV2 viral particles (from isolate 2019nCoV/italy-INMI1) in an oral swab-UTM matrix was tested at doses ranging from $10^{-5}$ to $10^{-8}$ $TCID_{50}$/mL. As reported in Table 3 and Table 4, relative to the detection of either ORF1ab sequences or S gene sequences, the use of both sets of preferred primers and probes was found to increase the sensitivity of the assay, achieving the detection of the $10^{-8}$ $TCID_{50}$/mL dose instead of $10^{-7}$ $TCID_{50}$/mL.

TABLE 3

| Samples | | | ORF1ab | S Gene | |
|---|---|---|---|---|---|
| Reps | $TCID_{50}$/mL | Copies/mL | Target | Target | Result |
| 1-40 | $10^{-7}$ | 4000 | Detected | Detected | Positive |
| 1-3 | $10^{-8}$ | 400 | Detected | Detected | Positive |
| 4 | | | Detected | Not Detected | Positive |
| 5 | | | Not Detected | Detected | Positive |
| 6 | | | Not Detected | Not Detected | Negative |
| 7 | | | Detected | Detected | Positive |
| 8 | | | Not Detected | Detected | Positive |
| 9 | | | Detected | Detected | Positive |
| 10 | | | Not Detected | Not Detected | Negative |
| 11 | | | Detected | Not Detected | Positive |
| 12-13 | | | Detected | Detected | Positive |
| 14 | | | Not Detected | Detected | Positive |
| 15-18 | | | Detected | Detected | Positive |
| 19 | | | Not Detected | Not Detected | Negative |

The results obtained at $10^{-8}$ $TCID_{50}$/mL (400 copies/mL) are summarized in Table 4.

TABLE 4

(Assay Detection Capability at 400 viral RNA copies/mL)

| | ORF1ab | S Gene | ORF1ab and S Gene |
|---|---|---|---|
| Number of Replicates Detected | 13/19 | 14/19 | 16/19 |
| Percentage of Detection | 68% | 73.7% | 84.2% |

The data used in Table 4 was based on a viral dose of $10^{-8}$ $TCID_{50}$/mL (400 copies/mL). When the samples contained 500 viral RNA copies/mL, the assays of the present invention exhibited a 100% ability to detect SARS-CoV-2 (Table 5).

TABLE 5

(Assay Detection Capability at 500 viral RNA copies/mL)

| | ORF1ab | S Gene | ORF1ab and S Gene |
|---|---|---|---|
| Number of Replicates Detected | 34/47 | 46/48 | 48/48 |
| Percentage of Detection | 72.3% | 95.8% | 100% |

This level of sensitivity (determined with genomic viral RNA) reflects the type of results one would obtain using clinical samples containing SARS-CoV-2. The assays of the present invention thus will provide healthcare workers with analytical indications that will enable them to better interpret the results of the assay in clinical practice.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. An oligonucleotide, having a 5' terminus and a 3' terminus, wherein said oligonucleotide is detectably labeled and has a nucleotide sequence that consists essentially of the nucleotide sequence of SEQ ID NO:9, SEQ ID NO:10, SEQ ID NO:11 or SEQ ID NO:12.

2. The oligonucleotide of claim 1, wherein said oligonucleotide has a nucleotide sequence that consists essentially of the nucleotide sequence of SEQ ID NO:9.

3. The oligonucleotide of claim 1, wherein said oligonucleotide has a nucleotide sequence that consists essentially of the nucleotide sequence of SEQ ID NO:10.

4. The oligonucleotide of claim 1, wherein said oligonucleotide has a nucleotide sequence that consists essentially of the nucleotide sequence of SEQ ID NO:11.

5. The oligonucleotide of claim 1, wherein said oligonucleotide has a nucleotide sequence that consists essentially of the nucleotide sequence of SEQ ID NO:12.

6. The oligonucleotide of claim 1, wherein said oligonucleotide has a nucleotide sequence that consists essentially of the nucleotide sequence of SEQ ID NO:9 or SEQ ID NO:10, wherein said oligonucleotide has a 5' terminus that is labeled with a fluorophore and a 3' terminus that is complexed to a quencher of fluorescence of said fluorophore.

7. The oligonucleotide of claim 1, wherein said oligonucleotide has a nucleotide sequence that consists essentially of the nucleotide sequence of SEQ ID NO:11 or SEQ ID NO:12, wherein said oligonucleotide has a 5' terminus that is labeled with a fluorophore and a 3' terminus that is complexed to a quencher of fluorescence of said fluorophore.

8. A method for detecting the presence of SARS-CoV-2 in a clinical sample, wherein said method comprises:

(I) incubating said clinical sample in vitro in the presence of:

(1) a reverse transcriptase and a DNA polymerase; and (2) a Forward ORF1ab Primer having a nucleotide sequence that consists essentially of the nucleotide sequence of SEQ ID NO:1;

(3) a Reverse ORF1ab Primer having a nucleotide sequence that consists essentially of the nucleotide sequence of SEQ ID NO:2; and (4) an ORF1ab Probe, said ORF1ab Probe being an oligonucleotide that is able to specifically hybridize to an oligonucleotide having a nucleotide sequence that consists essentially of the nucleotide sequence of SEQ ID NO:3 or SEQ ID NO:4, wherein said ORF1ab Probe oligonucleotide is labeled with a fluorophore and a quencher of fluorescence of said fluorophore;

wherein said incubation is in a reaction under conditions sufficient to permit:

(a) said Forward and Reverse ORF1ab Primers to mediate a polymerase chain reaction amplification of a region of the ORF1ab of SARS-CoV-2 to thereby produce an amplified ORF1ab oligonucleotide molecule, if said SARS-CoV-2 is present in said clinical sample;

(b) said ORF1ab Probe to hybridize to said amplified ORF1ab oligonucleotide molecules; and (c) (1) said DNA polymerase has a 5'→3' exonuclease activity that hydrolyzes said hybridized ORF1ab Probe, to thereby separate said fluorophore thereof from said quencher thereof and cause a fluorescent signal to become detectable; or (2) said hybridization of said ORF1ab Probe to said amplified ORF1ab oligonucleotide molecule separates said fluorophore thereof from said quencher thereof and causes a fluorescent signal to become detectable; and (II) determining whether said SARS-CoV-2 is present in said clinical sample by determining whether a fluorescent signal of said fluorophore has become detectable.

9. The method of claim 8, wherein said fluorophore has an excitation wavelength within the range of about 352-690 nm and an emission wavelength within the range of about 447-705 nm.

10. The method of claim 9, wherein said fluorophore is JOE or FAM.

11. A method for detecting the presence of SARS-CoV-2 in a clinical sample, wherein said method comprises:

(I) incubating said clinical sample in vitro in the presence of:

(1) a reverse transcriptase and a DNA polymerase; and (2) a Forward S Gene Primer having a nucleotide sequence that consists essentially of the nucleotide sequence of SEQ ID NO:5;

(3) a Reverse S Gene Primer having a nucleotide sequence that consists essentially of the nucleotide sequence of SEQ ID NO:6; and (4) an S Gene Probe, said S Gene Probe being an oligonucleotide that is able to specifically hybridize to an oligonucleotide having a nucleotide sequence that consists essentially of the nucleotide sequence of SEQ ID NO:7 or SEQ ID NO:8, wherein said S Gene Probe oligonucleotide is labeled with a fluorophore and a quencher of fluorescence of said fluorophore;

wherein said incubation is in a reaction under conditions sufficient to permit:

(a) said Forward and Reverse S Gene Primers to mediate a polymerase chain reaction amplification of a region of the S gene of SARS-CoV-2 to thereby produce an amplified S gene oligonucleotide molecules, if said SARS-CoV-2 is present in said clinical sample;

(b) said S Gene Probe to hybridize to said amplified S gene oligonucleotide molecule; and (c) (1) said DNA polymerase has a 5'→3' exonuclease activity that hydrolyzes said hybridized S Gene Probe, to thereby separate said fluorophore thereof from said quencher thereof and cause a fluorescent signal to become detectable; or (2) said hybridization of said S Gene Probe to said amplified S Gene oligonucleotide molecule separates said fluorophore thereof from said quencher thereof and causes a fluorescent signal to become detectable; and (II) determining whether said SARS-CoV-2 is present in said clinical sample by determining whether a fluorescent signal of said fluorophore has become detectable.

12. The method of claim 11, wherein said fluorophore has an excitation wavelength within the range of about 352-690 nm and an emission wavelength within the range of about 447-705 nm.

13. The method of claim 12, wherein said fluorophore is JOE or FAM.

14. The method of claim 11, wherein said clinical sample is incubated in the additional presence of:

(5) a Forward ORF1 ab Primer having a nucleotide sequence that consists essentially of the nucleotide sequence of SEQ ID NO:1;

(6) a Reverse ORF1ab Primer having a nucleotide sequence that consists essentially of the nucleotide sequence of SEQ ID NO:2; and (7) an ORF1ab Probe, said ORF1ab Probe being an oligonucleotide that is able to specifically hybridize to an oligonucleotide having a nucleotide sequence that consists essentially of the nucleotide sequence of SEQ ID NO:3 or SEQ ID NO:4, wherein said ORF1ab Probe oligonucleotide is labeled with a fluorophore and to a quencher of fluorescence of said fluorophore; wherein the fluorescence of said fluorophore of said ORF1ab Probe is distinguishable from the fluorescence of said fluorophore of said S Gene Probe;

wherein said reaction is additionally incubated under conditions sufficient to permit:

(a) said Forward and Reverse ORF1ab Primers to mediate a polymerase chain reaction amplification of a region of the ORF1ab of SARS-CoV-2 to thereby produce an amplified ORF1ab oligonucleotide molecule, if said SARS-CoV-2 is present in said clinical sample;

(b) said ORF1ab Probe to hybridize to said amplified ORF1ab oligonucleotide molecules; and (c) (1) said DNA polymerase has a 5'→3' exonuclease activity that hydrolyzes said hybridized ORF1ab Probe, to thereby separate said fluorophore thereof from said quencher thereof and cause a fluorescent signal to become detectable; or (2) said hybridization of said ORF1ab Probe to said amplified ORF1ab oligonucleotide molecule separates said fluorophore thereof from said quencher thereof and causes a fluorescent signal to become detectable; and wherein said SARS-CoV-2 is determined to be present in said clinical sample by determining whether a fluorescent signal of at least one of said ORF1ab Probe or said S Gene Probe fluorophores has become detectable.

15. The method of claim 11, wherein said fluorophore of said ORF1ab Probe and said fluorophore of said S Gene Probe have an excitation wavelength within the range of about 352-690 nm and an emission wavelength within the range of about 447-705 nm.

16. The method of claim 14, wherein one of said fluorophores of said ORF1ab Probe and said S Gene Probe is JOE and the other of such fluorophores is FAM.

17. A kit for detecting the presence of SARS-CoV-2 in a clinical sample, wherein said kit comprises:

(I) reagents for detecting SARS-CoV-2 ORF1ab, wherein said SARS-CoV-2 ORF1ab detection reagents comprise:

(1) a Forward ORF1ab Primer oligonucleotide having a nucleotide sequence that consists essentially of the nucleotide sequence of SEQ ID NO:1;

(2) a Reverse ORF1ab Primer oligonucleotide having a nucleotide sequence that consists essentially of the nucleotide sequence of SEQ ID NO:2; and (3) an ORF1ab Probe, said ORF1ab Probe being an oligonucleotide that is able to specifically hybridize to an oligonucleotide having a nucleotide sequence that consists essentially of the nucleotide sequence of SEQ ID NO:3 or SEQ ID NO:4, wherein said ORF1ab Probe oligonucleotide is labeled with a fluorophore and a quencher of fluorescence of said fluorophore;

and/or (II) reagents for detecting SARS-CoV-2 S gene, wherein said SARS-CoV-2 S gene detection reagents comprise:

(1) a Forward S Gene Primer oligonucleotide having a nucleotide sequence that consists essentially of the nucleotide sequence of SEQ ID NO:5;

(2) a Reverse S Gene Primer oligonucleotide having a nucleotide sequence that consists essentially of the nucleotide sequence of SEQ ID NO:6; and (3) an S Gene Probe, said S Gene Probe being an oligonucleotide that is able to specifically hybridize to an oligonucleotide having a nucleotide sequence that consists essentially of the nucleotide sequence of SEQ ID NO:7 or SEQ ID NO:8, wherein said S Gene Probe oligonucleotide is labeled with a fluorophore and a quencher of fluorescence of the fluorophore; wherein the fluorescence of said fluorophore of said S Gene Probe is distinguishable from the fluorescence of said fluorophore of said ORF1ab Probe.

18. The kit of claim 17, wherein said fluorophore of said ORF1ab Probe and said fluorophore of said S Gene Probe have an excitation wavelength within the range of about 352-690 nm and an emission wavelength within the range of about 447-705 nm.

19. The kit of claim 17, wherein said kit comprises both said SARS-CoV-2 ORF1ab detection reagents and said SARS-CoV-2 S gene detection reagents.

20. The kit of claim 19, wherein said fluorophore of said ORF1ab Probe and said fluorophore of said S Gene Probe have an excitation wavelength within the range of about 352-690 nm and an emission wavelength within the range of about 447-705 nm.

21. The kit of claim 20, wherein one of said fluorophores of said ORF1ab Probe and said S Gene Probe is JOE and the other of such fluorophores is FAM.

22. The method of claim 8, wherein said ORF1ab Probe has a nucleotide sequence that consists essentially of the nucleotide sequence of SEQ ID NO:9 or SEQ ID NO:10, and said DNA polymerase has said 5'→3' exonuclease activity that hydrolyzes hybridized ORF1ab Probe, to thereby separate said fluorophore thereof from said quencher thereof and cause a fluorescent signal to become detectable.

23. The method of claim 11, wherein said S Gene Probe has a nucleotide sequence that consists essentially of the nucleotide sequence of SEQ ID NO:11 or SEQ ID NO:12, and said DNA polymerase has said 5'→3' exonuclease activity that hydrolyzes hybridized S Gene Probe, to thereby separate said fluorophore thereof from said quencher thereof and cause a fluorescent signal to become detectable.

24. The method of claim 23, wherein said ORF1ab Probe has a nucleotide sequence that consists essentially of the nucleotide sequence of SEQ ID NO:9 or SEQ ID NO:10, and said DNA polymerase hydrolyzes hybridized ORF1ab Probe, to thereby separate said fluorophore thereof from said quencher thereof and cause a fluorescent signal to become detectable.

25. The kit of claim 17, wherein said ORF1ab Probe has a nucleotide sequence that consists essentially of the nucleotide sequence of SEQ ID NO:9 or SEQ ID NO:10.

26. The kit of claim 17, wherein said S Gene Probe has a nucleotide sequence that consists essentially of the nucleotide sequence of SEQ ID NO:11 or SEQ ID NO:12.

27. The kit of claim 17, wherein said kit comprises said SARS-CoV-2 ORF1ab detection reagents.

28. The kit of claim 27, wherein said ORF1ab Probe has a nucleotide sequence that consists essentially of the nucleotide sequence of SEQ ID NO:9 or SEQ ID NO:10.

29. The kit of claim 17, wherein said kit comprises said SARS-CoV-2 S gene detection reagents.

30. The kit of claim 29, wherein said S Gene Probe has a nucleotide sequence that consists essentially of the nucleotide sequence of SEQ ID NO:11 or SEQ ID NO:12.

* * * * *